United States Patent
Casolari et al.

(10) Patent No.: US 11,891,662 B2
(45) Date of Patent: Feb. 6, 2024

(54) POLYNUCLEOTIDES FOR AMPLIFICATION AND DETECTION OF HUMAN BETA ACTIN

(71) Applicant: Talis Biomedical Corporation, Redwood City, CA (US)

(72) Inventors: Jason M. Casolari, San Francisco, CA (US); Xuewen Jiang, Foster City, CA (US); Hédia Maamar, San Jose, CA (US)

(73) Assignee: Talis Biomedical Corporation, Redwood City, CA (US)

( * ) Notice: Subject to any disclaimer, the term of this patent is extended or adjusted under 35 U.S.C. 154(b) by 183 days.

(21) Appl. No.: 16/700,824

(22) Filed: Dec. 2, 2019

(65) Prior Publication Data

US 2021/0164043 A1    Jun. 3, 2021

(51) Int. Cl.
  *C12Q 1/68* (2018.01)
  *C12Q 1/6876* (2018.01)
  *C12Q 1/6816* (2018.01)
  *C12Q 1/6806* (2018.01)

(52) U.S. Cl.
  CPC ......... *C12Q 1/6876* (2013.01); *C12Q 1/6806* (2013.01); *C12Q 1/6816* (2013.01)

(58) Field of Classification Search
  None
  See application file for complete search history.

(56) References Cited

U.S. PATENT DOCUMENTS

| | | |
|---|---|---|
| 5,155,018 A | 10/1992 | Gillespie et al. |
| 5,234,809 A | 8/1993 | Boom et al. |
| 5,512,445 A | 4/1996 | Yang et al. |
| 5,804,141 A | 9/1998 | Chianese |
| 5,830,643 A | 11/1998 | Yamamoto et al. |
| 6,001,611 A | 12/1999 | Will |
| 6,383,393 B1 | 5/2002 | Colpan et al. |
| 7,504,111 B2 | 3/2009 | Fontana et al. |
| 7,728,119 B2 | 6/2010 | Nakamura et al. |
| 7,897,744 B2 | 3/2011 | Plummer et al. |
| 8,993,718 B2 | 3/2015 | Gross et al. |
| 9,187,789 B2 | 11/2015 | Pabich et al. |
| 9,434,999 B1 | 9/2016 | Ao et al. |
| 9,982,312 B2 | 5/2018 | Pearce et al. |
| 10,252,264 B2 | 4/2019 | Shen et al. |
| 10,450,616 B1 | 10/2019 | Dedent et al. |
| 10,954,572 B2 | 3/2021 | Dedent et al. |
| 11,047,007 B1 | 6/2021 | Andini et al. |
| 11,326,214 B2 | 5/2022 | Dedent et al. |
| 2004/0132218 A1 | 7/2004 | Ho |
| 2006/0216212 A1 | 9/2006 | Lum et al. |
| 2006/0257874 A1 | 11/2006 | Tisi et al. |
| 2007/0061898 A1 | 3/2007 | Yang et al. |
| 2007/0202523 A1 | 8/2007 | Becker et al. |
| 2008/0152587 A1 | 6/2008 | Zhou et al. |
| 2008/0276335 A1 | 11/2008 | Abad et al. |
| 2008/0299567 A1 | 12/2008 | Marshall et al. |
| 2008/0318282 A1 | 12/2008 | Uematsu et al. |
| 2009/0226885 A1 | 9/2009 | Sillekens et al. |
| 2009/0253622 A1 | 10/2009 | Van Noort et al. |
| 2010/0021886 A1 | 1/2010 | Wang et al. |
| 2012/0100551 A1 | 4/2012 | Kojima et al. |
| 2013/0017539 A1 | 1/2013 | Singhal et al. |
| 2013/0265054 A1 | 10/2013 | Lowery et al. |
| 2013/0323738 A1 | 12/2013 | Tanner et al. |
| 2014/0072971 A1 | 3/2014 | Wuitschick et al. |
| 2014/0308663 A1 | 10/2014 | Yonekawa et al. |
| 2014/0349295 A1 | 11/2014 | Hosaka et al. |
| 2015/0159205 A1 | 6/2015 | Narayanan et al. |
| 2015/0267266 A1 | 9/2015 | Soetaert et al. |
| 2015/0322493 A1 | 11/2015 | Tulp et al. |
| 2016/0024562 A1 | 1/2016 | Pabich et al. |
| 2016/0076083 A1 | 3/2016 | Ellington et al. |
| 2016/0257998 A1 | 9/2016 | Persing et al. |
| 2016/0273029 A1 | 9/2016 | Suwara et al. |
| 2016/0289730 A1 | 10/2016 | Pezacki et al. |
| 2016/0319378 A1 | 11/2016 | Rey |
| 2017/0283884 A1* | 10/2017 | Knudsen .............. A61K 31/436 |
| 2019/0111423 A1 | 4/2019 | Ismagilov et al. |
| 2019/0284617 A1 | 9/2019 | Lee et al. |
| 2019/0284618 A1 | 9/2019 | Dedent et al. |
| 2021/0254139 A1 | 8/2021 | Dedent et al. |
| 2021/0292854 A1 | 9/2021 | Andini et al. |

(Continued)

FOREIGN PATENT DOCUMENTS

| | | |
|---|---|---|
| CN | 101305101 A | 11/2008 |
| CN | 101831488 A | 9/2010 |

(Continued)

OTHER PUBLICATIONS

Lowe et al. A computer program for selection of oligonucleotide primers for polymerase chain reactions. Nucleic Acids Research, vol. 18(7), p. 1757-1761, 1990.*

Bakheit et al.; Sensitive and specific detection of *Cryptosporidium* species in PCR-negative samples by loop-mediated isothermal DNA amplification and confirmation of generated LAMP products by sequencing; Veterinary Parasitology; 158(1-2); pp. 11-22; Nov. 2008.

Beaucage et al.; Deoxynucleoside phosphoramidites—a new class of key intermediates for deoxypolynucleotide synthesis; Tetrahedron Letters; 22(20); pp. 1859-1862; Jan. 1981.

Broude; Stem-loop oligonucleotides: a robust tool for molecular biology and biotechnology; Trends in Biotechnology; 20(6); pp. 249-256; Jun. 2002.

Cady; Quantum dot molecular beacons for DNA detection; Micro and Nano Technologies in Bioanalysis; 554; pp. 367-379; 2009 (the year of publication is sufficiently earlier than the effective U.S. filing date and any foreign priority date so that the particular month of publication is not in issue).

(Continued)

*Primary Examiner* — Suryaprabha Chunduru
(74) *Attorney, Agent, or Firm* — Shay Glenn LLP

(57) ABSTRACT

Disclosed herein are primers and probes related to the detection of beta actin [*Homo sapiens* (human)] via nucleic acid amplification testing (NAAT), for example to amplify and determine the presence of β-actin present in test samples. Specifically, the present disclosure describes primers and probes that bind to the beta actin gene for detection via loop mediated isothermal amplification (LAMP) and molecular beacon hybridization.

8 Claims, No Drawings

Specification includes a Sequence Listing.

(56) References Cited

U.S. PATENT DOCUMENTS

| | | |
|---|---|---|
| 2021/0340622 A1 | 11/2021 | Andini et al. |
| 2022/0251630 A1 | 8/2022 | Dedent et al. |

FOREIGN PATENT DOCUMENTS

| | | |
|---|---|---|
| CN | 101886122 A | 11/2010 |
| CN | 102918155 A | 2/2013 |
| CN | 107099618 A | 8/2017 |
| JP | 2012130290 A | 7/2012 |
| JP | 5710190 B2 | 4/2015 |
| JP | 2017038572 A | 2/2017 |
| WO | WO2006/133385 A2 | 12/2006 |
| WO | WO2009/099037 A1 | 8/2009 |
| WO | WO2010/010951 A1 | 1/2010 |
| WO | WO2011/091330 A1 | 7/2011 |
| WO | WO2011/144304 A1 | 11/2011 |
| WO | WO2012/021802 A2 | 2/2012 |
| WO | WO2015/058008 A2 | 4/2015 |
| WO | WO2016/011280 A1 | 1/2016 |
| WO | WO2016/085632 A2 | 6/2016 |
| WO | WO2017/103269 A1 | 6/2017 |
| WO | WO2017/192902 A1 | 11/2017 |
| WO | WO2018/031531 A1 | 2/2018 |
| WO | WO2021/016602 A1 | 1/2021 |
| WO | WO2021/113267 A1 | 6/2021 |

OTHER PUBLICATIONS

Choopara et al.; Development of chlamydia trachomatis detection by loop-mediated isothermal amplification; International Journal of Biomedical Sciences and Bioformatics; 2(1); pp. 21-25; 2015 (the year of publication is sufficiently earlier than the effective U.S. filing date and any foreign priority date so that the particular month of publication is not in issue).

Choopara et al.; Rapid and visual chlamydia trachomatis detection using loop-mediated isothermal amplification and hydroxynaphthol blue; Letters in Applied Microbiology; 64(1); pp. 51-56; Sep. 2016.

Cissell et al.; Resonance energy transfer methods of RNA detection; Analytical and Bioanalytical Chenistry; 393(1); pp. 125-135; Jan. 2009.

Edwards et al.; Loop-mediated isothermal amplification test for detection of neisseria gonorrhoeae in urine samples and tolerance of the assay to the presence of urea; Journal of Clinical Microbiology; 52(6); pp. 2163-2165; Jun. 2014.

Eiken Chemical Co.; A guide to LAMP primer designing, Primer-Explorer V4; 19 pages; retrieved from the internet(https://primerexplorer.jp/e/v4_manual/pdf/PrimerExplorerV4_Manual_1.pdf) on Oct. 20, 2022.

Fan et al.; The Development and evaluation of a loop-mediated isothermal amplification method for the rapid detection of *Salmonella enterica* serovar typhi; Plos One; 10(4); eo124507; 13 pages; Apr. 2015.

Gandelman et al.; Loop-mediated amplification accelerated by stem primers; International Journal of Molecular Sciences; pp. 9108-9124; Dec. 2011.

GenBank Accession No. X67293, N. gonorrhoeae gene for 23S rRNA, 2pages; retrieved from the internet (https:ncbi.nlm.nih.gov/nucleotide/X67293.1?report=genobank&log$=nuclalign&blast_rank=95&RID=XZXX9U6R016) on Jan. 13, 2022.

GenBank submission AC127341.3; Mus musculus BAC clone RP23-189L19 from chromosome 17, complete sequence; Nov. 23, 2003 [Online]; 2 pages; retrieved from the internet (https://www.ncbi.nlm.nih/nuccore/AC127341) on Jul. 29, 2021.

GenBank submission AE004969.1. Neisseria gonorrhoeae FA 1090 complete genome, 2 pages; Jul. 1, 2015 [online]; retrieved from the internet (https://www.ncbi.nlm.nih.gov/nuccore/AE004969) on Nov. 23, 2020.

GenBank submission AFY24545.1; glycoprotien 5 (Porcine reproductive and respiratory syndrome virus; Feb. 28, 2013 [online]; 2 pages; retrieved from the internet (https://www.ncbi.nim.gov/prtein/AFY24545) on Jul. 29, 2021.

GenBank submission AL16244.1; Tetraodon nigroviridis genome survey sequence PC-Ori end clone 198J04 of library G from Tetraodon nigroviridis, genomic survey sequence, Sep. 1, 2000 [online] 2 pages; retrieved from the internet (https://www.ncbi.nlm.nih.gov/nuccore/AL169244) on Jul. 29, 2021.

GenBank submission CP019169.1; Betaproteobacteria bacterium GR16-43 chromosome, complete genome; Jan. 17, 2017 [online]; 2 pages; retrieved from the internet (https://www.ncbi.nim.nih.gov/nuccore/CP019169) on Jul. 29, 2021.

GenBank submission CZ791141.1, OC_Ba0158F23.fOC_BaOryza coarctata genomic clone OC_Ba158F23 5', genomic survey sequence; Aug. 29, 2012 [online]; 2 pages; retrieved from the internet (https://www.ncbi.nim.nih.gov/nuccore/CZ791141.1) on Jul. 29, 2021.

GenBank submission EK565433.1, 1095521038908 Global-Ocen-Sampling_GS-32-01-01-1P3-1P6KB marine metagenome genomic clone 1061005966854 5' genomic survey sequence, 2 pages; May 26, 2010 [online]; retrieved from the internet (https://www.ncbi.nlm.nih.gov/nuccore/EK565433 on Nov. 23, 2020.

GenBank submission HS475166 1, BL-57332 Nilaparvata lugens illumina library Nilaparvatalugens cDNA 5', mRNA sequence, May 3, 2011 [online]; 1 page; retrieved from the internet (https://www.ncbi.nlm.nih.gov/nuccore/HS475166) on Jul. 29, 2021.

GenBank submission LR606187.1; Aquila chrysaetos chrysaetos genome assembly, chromosome; Jul. 4, 2019 [online] 1 page; retrieved from the internet (https:/www.ncbi.nlm.nih.gov/nuccore/LR606187) on Nov. 23, 2020.

GenBank submission LS483369.1, Neisseria cinerea strain NCTC10294 genome assembly, chromosome: 1, Jun. 17, 2018 [online]; 1 page; retrieved from the internet (https://www.ncbi.nlm.nih.gov/nuccore/LS483369) on Nov. 23, 2020.

Iwamoto et al.; Loop-mediated isothermal amplification for direct detection of *Mycobacterium tuberculosis* complex m. avium, and m. intracellulare in sputum samples; Journal of clinical Microbiology; 41(6); pp. 2616-2622; Jun. 2003.

Jepsen et al.; Locked nucleic acid: potent nucleic acid analog in therapeutics and biotechnology; Oligonucleotides; 14(2); pp. 130-146; 2004 (the year of publication is sufficiently earlier than the effective U.S. filing date and any foreign priority date so that the particular month of publication is not in issue).

Jevtusevskaja et al.; Combination with antimicrobial peptide lyses improves loop-mediated isothermal amplification based method for chlamydia trachomatis detection directly in urine sample; BMC Infectious Diseases; 16(329); pp. 1-8; Jul. 2016.

Johns Hopkins University; Coronavirus resource center; 1 page; retrieved from the internet (https://coronavirus.jhu.edu/map.html) on Oct. 14, 2022.

Juskowiak; Nucleic acid-based fluorescent probes and their analytical potential; Analytical and Bioanalytical Chemistry; 399(9); pp. 3157-3176; Mar. 2011.

Katoh et al.; MAFFT multiple sequence alignment software version 7: improvements in performance and useability; Molecular Biology and Evolution; 30(4); pp. 772-780; Apr. 2013.

Lee et al.; Clinical evaluation of a loop-mediated isothermal amplification (LAMP) assay for rapid detection of neisseria meningitidis in cerebrospinal fluid; Plos One; 10(4); e0122922; 13 pages; Apr. 2015.

Li et al.; Molecular beacons: an optimal multifunctional biological probe; Biochemical and Biophysical Research Communications; 373(4); pp. 457-461; Sep. 2008.

Little et al.; Strand displacement amplification and homogeneous real-time detection incorporated in a second-generation dna probe system, BDProbe TecET; Clinical Chemistry; 45(6); pp. 777-784; Jun. 1999.

Liu et al.; Establishment of an accurate and fast detection method using molecular beacons in loop-mediated isothermal amplification assay; Scientific reports; 7(1); pp. 1-9; doi:10.1038/srep40125; Jan. 2017.

Liu et al.; Loop-mediated isothermal amplification of neisseria gonorrhoeae porA pseudogene: a rapid and reliable method to detect gonorrhea; AMB Express; 6; pp. 48; doi 10.1186/s13568-017-0349-6; 7 pages; Dec. 2017.

Nagamine et al.; Accelerated reaction by loop-mediated isothermal amplification using loop primers; 16(3); pp. 223-229; Jun. 2002.

(56) References Cited

OTHER PUBLICATIONS

Needham-Vandevanter et al.; Characterization of an adduct between CC-1065 and a defined oligodeoxynucleotide duplex; Nucleic Acids Research.; 12(15); pp. 6159-6168; Aug. 1984.
Neejara et al.; Rapid detection and differentiation of dengue virus serotypes by NSI specific reverse transcription loop-mediated isothermal amplification (RT-LAMP) assay in patients presenting to a tertiary care hospital in Hyderabad India; Journal of Virological Methods; 211; pp. 22-31; Jan. 2015.
Ng et al.; The laboratory diagnosis of neisseria gonorrhoeae; Canadian Journal of Infectious Diseases and Medical Microbiology; 16(1); pp. 15-25; Oct. 2005.
Nixon et al.; A novel approach for evaluating the performance of real time quantitative loop-mediated isothermal amplification-based methods; Biomolecular Detection and Quantification; vol. 2; pp. 4-10; Dec. 2014.
Njiru; Loop-mediated isothermal amplification technology: towards point of care diagnostics; Plos Neglected Tropical Diseases; 6(6); e1572; 4 pages; Jun. 2012.
Sievers et al.; Fast, scaleable generation of high-quality protein multiple sequence alignments using clustal omega; Molecular Systems Biology; 7(1); 539; doi: 10.1038/msb.2011.75; 8 pages; 2011 (the year of publication is sufficiently earlier than the effective U.S. filing date and any foreign priority date so that the particular month of publication is not in issue).
Tanner et al.; Simultaneous multiple target detection in real-time loop-mediated isothermal amplification; Biotechniques; 53(2); pp. 81-89; Aug. 2012.
Trembizki; Direct real-time PCR-based detection of neisseria gonorrhoeae 23S rRNA mutations associated with azithromycin resistance; Journal of Antimicrobial Chemotherapy; 70(12); pp. 3244-3249; Dec. 2015.
Tyagi et al.; Multicolor molecular beacons for allele discrimination; Nature Biotechnology; 16(1); pp. 49-53; Jan. 1998.
Wang et al.; Molecular engineering of DNA: molecular beacons: Angewandle Chemie International Edition; 48(5); pp. 856-870; 34 pages; (Author Manuscript) Jan. 2009.
Wang et al.; Rapid and sensitive detection of *Shigella* spp. and *Salmonella* spp. by multiple endonuclease restriction real-time loop-mediated isothermal amplification technique; The Journal of Molecular Diagnostics; 17(4): pp. 392-401; Jul. 2015.
Wang et al.; Two methods for increased specificity and sensitivity in loop-mediated isothermal amplification; Molecules; 20(4); pp. 6048-6059; Apr. 2015.
Wong et al.; Loop-mediated isothermal amplification (LAMP) a versatile technique for detection of micro-organisms; Journal of Applied Microbiology; 124(3); pp. 626-643; Mar. 2018.
World Health Organization; The use of commercial loop-mediated isothermal amplification assay (TB-LAMP) for detection of tuberculosis; Expert Group meeting Report Geneva; vol. 2013; pp. 1-50; May 2013.
Xu et al.; A capillary-based multiplexed isothermal nucleic acid-based test for sexually transmitted diseases in patients; Chemical Communications; 52(82); pp. 12187-12190; Sep. 2016.
Xu et al.; Rapid ultrasonic isothermal amplification of DNA with multiplexed melting analysis—applications in the clinical diagnosis of sexually transmitted diseases; Chemical Communications; 51(13); pp. 2589-2592; Jan. 2015.
Yamamoto et al.; Molecular beacon aptamer fluoresces in the presence of Tat protein of HIV-1; Genes to Cells; 5(5); pp. 389-396; May 2000.
Yamamura et al.; Evaluation of a new rapid molecular diagnostic system for plasmodium falciparum combined with DNA filter paper, loop-mediated isothermal amplification, and melting curve analysis; Jpn J. Infect. Dis.; 62(1); pp. 20-25; Jan. 2009.
Zanoli et al.; Isothermal amplification methods for the detection of nucleic acids in microfluidic devices; Biosensors; 3(1); pp. 18-43; Dec. 2012.
Dedent et al.; U.S. Appl. No. 17/718,025 entitled Polynucleotides for the amplification and detection of chlamydia trachomatis; filed Apr. 11, 2022.
Casolari et al.; U.S. Appl. No. 17/778,486 entitled "Polynucleotides for the amplfication and detection of human beta actin," filed May 20, 2022.
GenBank Accession No. NC045512; Severe acute respiratory syndrome coronavirus 2 isolate Wuhan-Hu-1, complete genome; 2 pages; retrieved from the internet (https://www.ncbi.nlm.nih.gov/nuccore/NC_045512.2?report=genbank&from=26523&to=27191) on Apr. 7, 2023.
Marras et al.; Efficiencies of fluorescence resonance energy transfer and contact?mediated quenching in oligonucleotide probes; Nucleic acids research; 30(21); e122; 8 pages; Nov. 1, 2002.
Chui et al.; A comparison of three real-time PCR assays for the confirmation of Neisseria gonorrhoeae following detection of N. gonorrhoeae using Roche COBAS AMPLICOR. Clinical microbiology and infection; 14(5); pp. 473-479; May 1, 2008.
Falk et al.; Sampling for Chlamydia trachomatis infection comparison of vaginal, first-catch urine, combined vaginal and first-catch urine and endocervical sampling; International journal of STD & AIDS; 21(4); pp. 283-287; Apr. 2010.
Michel et al.; Chlamydia trachomatis load at matched anatomic sites: implications for screening strategies; Journal of clinical microbiology; 45(5); pp. 1395-1402; May 2007.
Notomi et al.; Loop-mediated isothermal amplification of DNA; Nucleic acids research; 28(12); e63; Jun. 15, 2000.
Papp et al.; Recommendations for the laboratory-based detection of Chlamydia trachomatis and Neisseria gonorrhoeae—2014; MMWR; Recommendations and reports: Morbidity and mortality weekly report. Recommendations and reports/Centers for Disease Control; 63(1): 19 pages; Mar. 3, 2014.
Priest et al.; Neisseria gonorrhoeae DNA bacterial load in men with symptomatic and asymptomatic gonococcal urethritis; Sexually Transmitted Infections ;93(7); pp. 478-481; Nov. 1, 2017.
Dedent et al.; U.S. Appl. No. 18/296,978 entitled "Polynucleotides for the amplification and detection of neisseria gonorrhoeae," filed Apr. 6, 2023.
Kubota et al.; FRET-based assimilating probe for sequence-specific real-time monitoring of loop-mediated isothermal amplification (LAMP); Biological Engineering Transactions; 4(2); pp. 81-100; Jan. 2011.
Kimura et al.; Point of care testing chip for multiple virus infection detection using LAMP; 2019 IEEE 32nd International Conference on Micro Electro Mechanical Systems (MEMS); pp. 83-86; Jan. 27, 2019.

\* cited by examiner

POLYNUCLEOTIDES FOR AMPLIFICATION AND DETECTION OF HUMAN BETA ACTIN

SEQUENCE LISTING

The instant application contains a Sequence Listing which has been submitted electronically in ASCII format and is hereby incorporated by reference in its entirety. Said ASCII copy, created on Jan. 31, 2020, is named TSM-047US SL.txt and is 42,568 bytes in size.

FIELD OF THE INVENTION

The present invention relates to the fields of molecular biology and nucleic acid chemistry. The invention provides methods and reagents for detecting mammalian, specifically human, gene for beta actin and also relates to the fields of medical diagnostics and prognostics. In particular, the invention relates to polynucleotides and methods for amplifying and detecting beta actin, hereinafter referred to as "β-actin".

BACKGROUND

Housekeeping genes are required for the maintenance of basal cellular functions essential for the existence of a cell, regardless of its specific role in the tissue or organism. Thus, such genes are expected to be expressed in all cells of an organism under normal and patho-physiological conditions, irrespective of tissue type, developmental stage, cell cycle state, or external signal. Since these genes represent the minimal set of genes necessary for sustaining life, they can provide value to researchers and professionals conducting experimental studies and molecular testing by frequently using them as a control. Controls are assessed in parallel with target analytes of interest to establish a factor of confidence in the final results obtained. When the expected presence of the control is determined, one or more aspects of the experiment or assay are confirmed to be properly functioning. However, when the expected presence of the control is absent, the final results in question do not meet performance standards and indicate an error.

In one specific example, nucleic acid amplification tests (NAATs) for molecular diagnostic testing require the use of one or more controls to be tested and detected in parallel with one or more target analytes of interest. The embodiments disclosed herein provide primers and probes relate to the detection of the housekeeping gene encoding β-actin using loop-mediated isothermal amplification.

SUMMARY OF THE INVENTION

The present invention encompasses, in some embodiments, a composition comprising a set of polynucleotides selected from the group consisting of Set-1 through Set-29. In some embodiments, the composition further comprises a probe. In some embodiments, the probe comprises a label. In some embodiments, the probe is a labeled polynucleotide. In a preferred implementation, the label is a fluorophore, which preferably is covalently attached to a terminus of the polynucleotide. In a particularly preferred embodiment, the probe or polynucleotide is a molecular beacon comprising a fluorophore, a quencher, and a polynucleotide. In one embodiment, the fluorophore is FAM and the quencher is BHQ1. In an alternate implementation, the fluorophore is ATTO 565 or Alexa 594 and the quencher is BHQ1 or BHQ2.

In some implementations, composition comprises a labeled polynucleotide comprising a sequence selected from the group consisting of nucleotides 6-33 of SEQ ID NO: 135, nucleotides 6-30 of SEQ ID NO: 136, nucleotides 7-27 of SEQ ID NO: 137, nucleotides 7-26 of SEQ ID NO: 138, nucleotides 1-26 of SEQ ID NO: 139, nucleotides 7-26 of SEQ ID NO: 140, nucleotides 7-30 of SEQ ID NO: 141, nucleotides 6-30 of SEQ ID NO: 142, nucleotides 8-32 of SEQ ID NO: 143, nucleotides 8-30 of SEQ ID NO: 144, nucleotides 6-31 of SEQ ID NO: 145, nucleotides 8-30 of SEQ ID NO: 146, 8-22 of SEQ ID NO: 147, nucleotides 8-24 of SEQ ID NO: 148, nucleotides 7-27 of SEQ ID NO: 149, nucleotides 8-21 of SEQ ID NO: 150, nucleotides 8-32 of SEQ ID NO: 151, nucleotides 1-24 of SEQ ID NO: 152, nucleotides 4-24 of SEQ ID NO: 153, nucleotides 1-23 of SEQ ID NO: 154, nucleotides 8-26 of SEQ ID NO: 155, nucleotides 7-29 of SEQ ID NO: 156, nucleotides 8-28 of SEQ ID NO: 157, nucleotides 8-29 of SEQ ID NO: 158, nucleotides 7-25 of SEQ ID NO: 159, nucleotides 8-22 of SEQ ID NO: 160, nucleotides 6-22 of SEQ ID NO: 161, nucleotides 3-22 of SEQ ID NO: 162, nucleotides 8-28 of SEQ ID NO: 163, nucleotides 3-28 of SEQ ID NO: 164, nucleotides 5-25 of SEQ ID NO: 165, nucleotides 5-26 of SEQ ID NO: 166, nucleotides 5-20 of SEQ ID NO: 167, nucleotides 4-22 of SEQ ID NO: 168, nucleotides 7-22 of SEQ ID NO: 169, nucleotides 3-22 of SEQ ID NO: 170, nucleotides 7-28 of SEQ ID NO: 171, nucleotides 6-27 of SEQ ID NO: 172, nucleotides 7-29 of SEQ ID NO: 173, nucleotides 5-27 of SEQ ID NO: 174, nucleotides 7-29 of SEQ ID NO: 175, nucleotides 6-28 of SEQ ID NO: 176, nucleotides 4-23 of SEQ ID NO: 177, nucleotides 4-34 of SEQ ID NO: 178, nucleotides 3-27 of SEQ ID NO: 179, nucleotides 2-27 of SEQ ID NO: 180, nucleotides 5-33 of SEQ ID NO: 181, nucleotides 3-30 of SEQ ID NO: 182, nucleotides 9-34 of SEQ ID NO: 183, and nucleotides 8-28 of SEQ ID NO: 184. In further implementations, the labeled polynucleotide can comprise a sequence elected from the group consisting of SEQ ID NO: 135 through SEQ ID NO: 184. In certain implementations, the sequence of the labeled polynucleotide is selected from the group consisting of SEQ ID NO: 135 through SEQ ID NO: 184.

In some embodiments, the set of polynucleotides is selected from the group consisting of Sets 9-12, Set-17, and Sets 22-29, and the composition comprises a labeled polynucleotide comprising a sequence selected from the group consisting of nucleotides 8-22 of SEQ ID NO: 147, nucleotides 8-24 of SEQ ID NO: 148, nucleotides 7-27 of SEQ ID NO: 149, nucleotides 8-21 of SEQ ID NO: 150, nucleotides 8-26 of SEQ ID NO: 155, nucleotides 7-29 of SEQ ID NO: 156, nucleotides 5-25 of SEQ ID NO: 165, nucleotides 5-26 of SEQ ID NO: 166, nucleotides 5-20 of SEQ ID NO: 167, nucleotides 4-22 of SEQ ID NO: 168, nucleotides 7-22 of SEQ ID NO: 169, nucleotides 7-28 of SEQ ID NO: 171, nucleotides 6-27 of SEQ ID NO: 172, nucleotides 7-29 of SEQ ID NO: 173, nucleotides 5-27 of SEQ ID NO: 174, nucleotides 7-29 of SEQ ID NO: 175, nucleotides 6-28 of SEQ ID NO: 176, nucleotides 9-34 of SEQ ID NO: 183, and nucleotides 8-28 of SEQ ID NO: 184. In some implementations, the labeled polynucleotide comprises a sequence selected from the group consisting of SEQ ID NO: 147, SEQ ID NO: 148, SEQ ID NO: 149, SEQ ID NO: 150, SEQ ID NO: 155, SEQ ID NO: 156, SEQ ID NO: 165, SEQ ID NO: 166, SEQ ID NO: 167, SEQ ID NO: 168, SEQ ID NO: 169, SEQ ID NO: 171, SEQ ID NO: 172, SEQ ID NO: 173, SEQ ID NO: 174, SEQ ID NO: 175, SEQ ID NO: 176, SEQ ID NO: 183, and SEQ ID NO: 184. In some implementations, the sequence of the labeled polynucleotide is SEQ ID NO:

147, SEQ ID NO: 148, SEQ ID NO: 149, SEQ ID NO: 150, SEQ ID NO: 155, SEQ ID NO: 156, SEQ ID NO: 165, SEQ ID NO: 166, SEQ ID NO: 167, SEQ ID NO: 168, SEQ ID NO: 169, SEQ ID NO: 171, SEQ ID NO: 172, SEQ ID NO: 173, SEQ ID NO: 174, SEQ ID NO: 175, SEQ ID NO: 176, SEQ ID NO: 183, and SEQ ID NO: 184. In a preferred implementation, the sequence of the labeled polynucleotide is SEQ ID NO: 184, and the set of polynucleotides is Set-29.

In yet another embodiment, the set of polynucleotides is selected from the group consisting of Sets 9-11, Set-17, and Sets 23-29, and the composition comprises a labeled polynucleotide comprising a sequence selected from the group consisting of nucleotides 1-24 of SEQ ID NO: 152, nucleotides 4-24 of SEQ ID NO: 153, and nucleotides 1-23 of SEQ ID NO: 154. More particularly, the labeled polynucleotide can comprise a sequence selected from the group consisting of SEQ ID NO: 152, SEQ ID NO: 153, and SEQ ID NO: 154. In certain implementations, the sequence of the labeled polynucleotide is selected from the group SEQ ID NO: 152, SEQ ID NO: 153, and SEQ ID NO: 154.

In one implementation, the set of polynucleotides is selected from the group consisting of Set-4, Sets 9-12, Set-17, and Sets 22-26, and the composition comprises a labeled polynucleotide comprising a sequence selected from the group consisting of nucleotides 8-30 of SEQ ID NO: 144, nucleotides 6-31 of SEQ ID NO: 145, and nucleotides 8-30 of SEQ ID NO: 146. In certain implementations, the labeled polynucleotide comprises a sequence selected from the group consisting of SEQ ID NO: 144, SEQ ID NO: 145, and SEQ ID NO: 146. In some embodiments, the sequence of the labeled polynucleotide is selected from the group SEQ ID NO: 144, SEQ ID NO: 145, and SEQ ID NO: 146.

In another implementation, the set of polynucleotides is selected from the group consisting of Set-5, Set-12, Set-17, and Sets 22-25, and the composition comprises a labeled polynucleotide comprising nucleotides 3-22 of SEQ ID NO: 170. In some implementations, the labeled polynucleotide comprises SEQ ID NO: 170. In other embodiments, the sequence of the labeled polynucleotide is SEQ ID NO: 170.

In one embodiment, the set of polynucleotides is selected from the group consisting of Sets 6-8, Set-15, and Set-16, and the composition comprises a labeled polynucleotide comprising a sequence selected from the group consisting of nucleotides 2-27 of SEQ ID NO: 180 and nucleotides 3-30 of SEQ ID NO: 182. In some implementations, the labeled polynucleotide comprises a sequence selected from the group consisting of SEQ ID NO: 180 and SEQ ID NO: 182. In other embodiments the sequence of the labeled polynucleotide is SEQ ID NO: 180 or SEQ ID NO: 182.

In yet another embodiment, the set of polynucleotides is selected from the group consisting of Sets 6-11, Set-28, and Set-29, and the composition comprises a labeled polynucleotide comprising a sequence selected from the group consisting of nucleotides 4-34 of SEQ ID NO: 178 and nucleotides 5-33 of SEQ ID NO: 181. In some embodiments, the labeled polynucleotide comprises a sequence selected from the group consisting of SEQ ID NO: 178 and SEQ ID NO: 181. In other embodiments, the sequence of the labeled polynucleotide is SEQ ID NO: 178 or SEQ ID NO: 181.

In certain implementations, the set of polynucleotides is selected from the group consisting of Sets 6-9 and Set-11, and the composition comprises a labeled polynucleotide comprising nucleotides 3-27 of SEQ ID NO: 179. In other implementations, the labeled polynucleotide comprises SEQ ID NO: 179. In yet another implementation, the sequence of the labeled polynucleotide is SEQ ID NO: 179.

In one embodiment, the set of polynucleotides is selected from the group consisting of Sets 6-9, Set-11, and Set-28, and the composition comprises a labeled polynucleotide comprising nucleotides 4-23 of SEQ ID NO: 177. In some embodiments, the labeled polynucleotide comprises SEQ ID NO: 177. In other embodiments, the sequence of the labeled polynucleotide is SEQ ID NO: 177.

In one implementation, the set of polynucleotides is selected from the group consisting of Sets 13-15, and the composition comprises a labeled polynucleotide comprising a sequence selected from the group consisting of nucleotides 7-25 of SEQ ID NO: 159 and nucleotides 8-22 of SEQ ID NO: 160. In another implementation, the labeled polynucleotide comprises a sequence selected from the group consisting of SEQ ID NO: 159 and SEQ ID NO: 160. In other implementations, the sequence of the labeled polynucleotide is SEQ ID NO: 159 or SEQ ID NO: 160.

In one embodiment, the set of polynucleotides is selected from the group consisting of Sets 13-16, and the composition comprises a labeled polynucleotide comprising a sequence selected from the group consisting of nucleotides 8-28 of SEQ ID NO: 157, nucleotides 8-29 of SEQ ID NO: 158, nucleotides 6-22 of SEQ ID NO: 161, and nucleotides 3-22 of SEQ ID NO: 162. In such an embodiment, the labeled polynucleotide can comprise a sequence selected from the group consisting of SEQ ID NO: 157, SEQ ID NO: 158, SEQ ID NO: 161, and SEQ ID NO: 162. In yet another embodiment, the sequence of the labeled polynucleotide is selected from the group consisting of SEQ ID NO: 157, SEQ ID NO: 158, SEQ ID NO: 161, and SEQ ID NO: 162.

In another implementation, the set of polynucleotides is Set-3, and the composition comprises a labeled polynucleotide comprising a sequence selected from the group consisting of nucleotides 7-27 of SEQ ID NO: 137, nucleotides 7-26 of SEQ ID NO: 138, nucleotides 1-26 of SEQ ID NO: 139, nucleotides 7-26 of SEQ ID NO: 140, nucleotides 7-30 of SEQ ID NO: 141, nucleotides 6-30 of SEQ ID NO: 142, nucleotides 8-32 of SEQ ID NO: 151, and nucleotides 4-24 of SEQ ID NO: 153. In certain implementations, the labeled polynucleotide comprises a sequence selected from the group consisting of SEQ ID NO: 137, SEQ ID NO: 138, SEQ ID NO: 139, SEQ ID NO: 140, SEQ ID NO: 141, SEQ ID NO: 142, SEQ ID NO: 151, and SEQ ID NO: 153. In a further implementation, the sequence of the labeled polynucleotide is selected from the group consisting of SEQ ID NO: 137, SEQ ID NO: 138, SEQ ID NO: 139, SEQ ID NO: 140, SEQ ID NO: 141, SEQ ID NO: 142, SEQ ID NO: 151, and SEQ ID NO: 153.

In some embodiments, the set of polynucleotides is selected from the group consisting Set-1, Set-2, and Sets 18-20, and the composition comprises a labeled polynucleotide comprising a sequence selected from the group consisting of nucleotides 8-28 of SEQ ID NO: 163 and nucleotides 3-28 of SEQ ID NO: 164. In some implementations, the labeled polynucleotide comprises a sequence selected from the group consisting of SEQ ID NO: 163 and SEQ ID NO: 164. In other embodiments, the sequence of the labeled polynucleotide is SEQ ID NO: 163 or SEQ ID NO: 164.

In yet another implementation, the set of polynucleotides is selected from the group consisting of Set-1, Set-2 and Sets 18-21, and the composition comprises a labeled polynucleotide comprising a sequence selected from the group consisting of nucleotides 6-33 of SEQ ID NO: 135 and nucleotides 6-30 of SEQ ID NO: 136. In some embodiments, the labeled polynucleotide comprises a sequence from the group consisting of SEQ ID NO: 135 and SEQ ID NO: 136. In other embodiments, the sequence of the labeled polynucleotide is SEQ ID NO: 135 or SEQ ID NO: 136.

Another aspect of the invention provides molecular beacons comprising a fluorophore, a quencher, and a polynucleotide, wherein the polynucleotide comprises a sequence selected from the group consisting of nucleotides 6-33 of SEQ ID NO: 135, nucleotides 6-30 of SEQ ID NO: 136, nucleotides 7-27 of SEQ ID NO: 137, nucleotides 7-26 of SEQ ID NO: 138, nucleotides 1-26 of SEQ ID NO: 139, nucleotides 7-26 of SEQ ID NO: 140, nucleotides 7-30 of SEQ ID NO: 141, nucleotides 6-30 of SEQ ID NO: 142, nucleotides 8-32 of SEQ ID NO: 143, nucleotides 8-30 of SEQ ID NO: 144, nucleotides 6-31 of SEQ ID NO: 145, nucleotides 8-30 of SEQ ID NO: 146, 8-22 of SEQ ID NO: 147, nucleotides 8-24 of SEQ ID NO: 148, nucleotides 7-27 of SEQ ID NO: 149, nucleotides 8-21 of SEQ ID NO: 150, nucleotides 8-32 of SEQ ID NO: 151, nucleotides 1-24 of SEQ ID NO: 152, nucleotides 4-24 of SEQ ID NO: 153, nucleotides 1-23 of SEQ ID NO: 154, nucleotides 8-26 of SEQ ID NO: 155, nucleotides 7-29 of SEQ ID NO: 156, nucleotides 8-28 of SEQ ID NO: 157, nucleotides 8-29 of SEQ ID NO: 158, nucleotides 7-25 of SEQ ID NO: 159, nucleotides 8-22 of SEQ ID NO: 160, nucleotides 6-22 of SEQ ID NO: 161, nucleotides 3-22 of SEQ ID NO: 162, nucleotides 8-28 of SEQ ID NO: 163, nucleotides 3-28 of SEQ ID NO: 164, nucleotides 5-25 of SEQ ID NO: 165, nucleotides 5-26 of SEQ ID NO: 166, nucleotides 5-20 of SEQ ID NO: 167, nucleotides 4-22 of SEQ ID NO: 168, nucleotides 7-22 of SEQ ID NO: 169, nucleotides 3-22 of SEQ ID NO: 170, nucleotides 7-28 of SEQ ID NO: 171, nucleotides 6-27 of SEQ ID NO: 172, nucleotides 7-29 of SEQ ID NO: 173, nucleotides 5-27 of SEQ ID NO: 174, nucleotides 7-29 of SEQ ID NO: 175, nucleotides 6-28 of SEQ ID NO: 176, nucleotides 4-23 of SEQ ID NO: 177, nucleotides 4-34 of SEQ ID NO: 178, nucleotides 3-27 of SEQ ID NO: 179, nucleotides 2-27 of SEQ ID NO: 180, nucleotides 5-33 of SEQ ID NO: 181, nucleotides 3-30 of SEQ ID NO: 182, nucleotides 9-34 of SEQ ID NO: 183, and nucleotides 8-28 of SEQ ID NO: 184.

Yet another aspect of the invention provides method of detecting β-actin in a test sample, the method comprising (a) extracting nucleic acid from the test sample, (b) amplifying a target sequence by reacting the nucleic acid extracted in step (a) with a reaction mixture comprising a strand displacement DNA polymerase and a sequence specific primer set, wherein said sequence-specific primer set is selected from the group consisting of Set-1 through Set-29, and (c) detecting the presence or absence of an amplified product of step (b); wherein the presence of said amplification product is indicative of the presence of β-actin in the test sample. In one embodiment, the amplification in step (b) of the target sequence is performed between about 60° C. and about 67° C. for less than 30 minutes. Preferably, the amplification step is performed for less than fifteen minutes. In some implementations, the reaction mixture further comprises a reverse transcriptase.

In certain embodiments, detecting the presence or absence of the amplification product comprises hybridizing the amplified product with a probe comprising a polynucleotide attached to a label. In a preferred implementation, the label is a fluorophore, which is preferably attached to a terminus of the polynucleotide. In a particularly preferred embodiment, the probe or polynucleotide is a molecular beacon comprising a fluorophore, a quencher, and a polynucleotide. In one embodiment, the fluorophore is FAM and the quencher is BHQ1. In an alternate implementation, the fluorophore is ATTO 565 or Alexa 594 and the quencher is BHQ1 or BHQ2.

Yet another aspect of the invention provides kits comprising the compositions comprising a set of polynucleotides selected from the group consisting Set-1 through Set-29. In some embodiments, the kit further comprises a strand displacement polymerase and, optionally, a reverse transcriptase. In certain embodiments, the kit comprises a molecular beacon comprising a fluorophore, a quencher, and a polynucleotide, wherein the polynucleotide comprises a sequence selected from the group consisting of nucleotides 6-33 of SEQ ID NO: 135, nucleotides 6-30 of SEQ ID NO: 136, nucleotides 7-27 of SEQ ID NO: 137, nucleotides 7-26 of SEQ ID NO: 138, nucleotides 1-26 of SEQ ID NO: 139, nucleotides 7-26 of SEQ ID NO: 140, nucleotides 7-30 of SEQ ID NO: 141, nucleotides 6-30 of SEQ ID NO: 142, nucleotides 8-32 of SEQ ID NO: 143, nucleotides 8-30 of SEQ ID NO: 144, nucleotides 6-31 of SEQ ID NO: 145, nucleotides 8-30 of SEQ ID NO: 146, 8-22 of SEQ ID NO: 147, nucleotides 8-24 of SEQ ID NO: 148, nucleotides 7-27 of SEQ ID NO: 149, nucleotides 8-21 of SEQ ID NO: 150, nucleotides 8-32 of SEQ ID NO: 151, nucleotides 1-24 of SEQ ID NO: 152, nucleotides 4-24 of SEQ ID NO: 153, nucleotides 1-23 of SEQ ID NO: 154, nucleotides 8-26 of SEQ ID NO: 155, nucleotides 7-29 of SEQ ID NO: 156, nucleotides 8-28 of SEQ ID NO: 157, nucleotides 8-29 of SEQ ID NO: 158, nucleotides 7-25 of SEQ ID NO: 159, nucleotides 8-22 of SEQ ID NO: 160, nucleotides 6-22 of SEQ ID NO: 161, nucleotides 3-22 of SEQ ID NO: 162, nucleotides 8-28 of SEQ ID NO: 163, nucleotides 3-28 of SEQ ID NO: 164, nucleotides 5-25 of SEQ ID NO: 165, nucleotides 5-26 of SEQ ID NO: 166, nucleotides 5-20 of SEQ ID NO: 167, nucleotides 4-22 of SEQ ID NO: 168, nucleotides 7-22 of SEQ ID NO: 169, nucleotides 3-22 of SEQ ID NO: 170, nucleotides 7-28 of SEQ ID NO: 171, nucleotides 6-27 of SEQ ID NO: 172, nucleotides 7-29 of SEQ ID NO: 173, nucleotides 5-27 of SEQ ID NO: 174, nucleotides 7-29 of SEQ ID NO: 175, nucleotides 6-28 of SEQ ID NO: 176, nucleotides 4-23 of SEQ ID NO: 177, nucleotides 4-34 of SEQ ID NO: 178, nucleotides 3-27 of SEQ ID NO: 179, nucleotides 2-27 of SEQ ID NO: 180, nucleotides 5-33 of SEQ ID NO: 181, nucleotides 3-30 of SEQ ID NO: 182, nucleotides 9-34 of SEQ ID NO: 183, and nucleotides 8-28 of SEQ ID NO: 184. The polynucleotide sequence of the molecular beacon can comprise a sequence selected from the group consisting of SEQ ID NO: 135 through SEQ ID NO: 184. In some embodiments, the polynucleotide sequence of the molecular beacon consists of a sequence selected from the group consisting of SEQ ID NO: 135 through SEQ ID NO: 184. In one embodiment, the polynucleotide sequence of the molecular beacon consists of SEQ ID NO: 184 and the set of polynucleotides is Set-29.

Another aspect of the invention provides methods of detecting β-actin in a test sample, the method comprising (a) extracting nucleic acid from the test sample, (b) amplifying a target sequence by reacting nucleic acid extracted in step (a) for less than ten minutes with a reaction mixture comprising a strand displacement DNA polymerase and a sequence specific LAMP primer set, and (c) detecting the presence or absence of an amplified product of step (b); wherein the presence of said amplification product is indicative of the presence of β-actin in the test sample. In some implementations, the amplifying step comprises reacting the nucleic acid extracted in step (a) with a reaction mixture comprising a strand displacement DNA polymerase and a sequence-specific primer set, wherein said sequence-specific primer set is selected from the group consisting of Set-1 through Set-29. In such implementations, detecting the presence or absence of the amplification product can comprise hybridizing the amplified product with a molecular beacon comprising a polynucleotide sequence selected from the group consisting of SEQ ID NO: 135 through SEQ ID NO: 184. In such implementations, detecting the presence or absence of the amplification product comprises hybridizing the amplified product with a molecular beacon comprising a polynucleotide sequence selected from the group consisting of SEQ ID NO: 147, SEQ ID NO: 148, SEQ ID NO: 149, SEQ ID NO: 150, SEQ ID NO: 155, SEQ ID NO: 156, SEQ ID NO: 165, SEQ ID NO: 166, SEQ ID NO: 167, SEQ ID NO: 168, SEQ ID NO: 169, SEQ ID NO: 171, SEQ ID NO: 172, SEQ ID NO: 173, SEQ ID NO: 174, SEQ ID NO: 175, SEQ ID NO: 176, SEQ ID NO: 183, and SEQ ID NO: 184.

DETAILED DESCRIPTION

The present invention encompasses, in some embodiments, a composition comprising a set of polynucleotides for priming a nucleic acid amplification reaction and methods of using such. In some embodiments, the composition further comprises a probe.

As used herein, "nucleic acid" includes both DNA and RNA, including DNA and RNA containing non-standard nucleotides. A "nucleic acid" contains at least one polynucleotide (a "nucleic acid strand"). A "nucleic acid" may be single-stranded or double-stranded. The term "nucleic acid" refers to nucleotides and nucleosides which make up, for example, deoxyribonucleic acid (DNA) macromolecules and ribonucleic acid (RNA) macromolecules. The most common nucleic acids are deoxyribonucleic acid (DNA) and ribonucleic acid (RNA). It should be further understood that the present invention can be used for biological sequences containing artificial nucleotides such as peptide nucleic acid (PNA), morpholino, locked nucleic acid (LNA), glycol nucleic acid (GNA) and threose nucleic acid (TNA), among others. Preferably, the artificial nucleotides are locked nucleic acid molecules, including [alpha]-L-LNAs. LNAs comprise ribonucleic acid analogues wherein the ribose ring is "locked" by a methylene bridge between the 2'-oxygen and the 4'-carbon—i.e., oligonucleotides, containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)).

As used herein, a "polynucleotide" refers to a polymeric chain containing two or more nucleotides, which contain deoxyribonucleotides, ribonucleotides, and/or their analog, such as those containing modified backbones (e.g. peptide nucleic acids (PNAs) or phosphorothioates) or modified bases. "Polynucleotides" includes primers, oligonucleotides, nucleic acid strands, etc. A polynucleotide may contain standard or non-standard nucleotides. Thus the term includes mRNA, tRNA, rRNA, ribozymes, DNA, cDNA, recombinant nucleic acids, branched nucleic acids, plasmids, vectors, probes, primers, etc. Typically, a polynucleotide contains a 5' phosphate at one terminus ("5' terminus") and a 3' hydroxyl group at the other terminus ("3' terminus") of the chain. The most 5' nucleotide of a polynucleotide may be referred to herein as the "5' terminal nucleotide" of the polynucleotide. The most 3' nucleotide of a polynucleotide may be referred to herein as the "3' terminal nucleotide" of the polynucleotide. Where nucleic acid of the invention takes the form of RNA, it may or may not have a 5' cap.

LAMP is a nucleic acid amplification method that relies on auto-cycle strand-displacement DNA synthesis performed by Bst DNA polymerase, or other strand displacement polymerases. The amplified products are stem-loop structures with several repeated sequences of the target, and have multiple loops. The principal merit of this method is that denaturation of the DNA template is not required, and thus the LAMP reaction can be conducted under isothermal conditions (ranging from 60 to 67° C.). LAMP requires only one enzyme and four types of primers that recognize six distinct hybridization sites in the target sequence. The reaction can be accelerated by the addition of two additional primers. The method produces a large amount of amplified product, resulting in easier detection, such as detection by visual judgment of the turbidity or fluorescence of the reaction mixture.

In brief, the reaction is initiated by annealing and extension of a pair of 'loop-forming' primers (forward and backward inner primers, FIP and BIP, respectively), followed by annealing and extension of a pair of flanking primers (F3 and B3). Extension of these primers results in strand-displacement of the loop-forming elements, which fold up to form terminal hairpin-loop structures. Once these key structures have appeared, the amplification process becomes self-sustaining, and proceeds at constant temperature in a continuous and exponential manner (rather than a cyclic manner, like PCR) until all of the nucleotides (dATP, dTTP, dCTP & dGTP) in the reaction mixture have been incorporated into the amplified DNA. Optionally, an additional pair of primers can be included to accelerate the reaction. These primers, termed Loop primers, hybridize to non-inner primer bound terminal loops of the inner primer dumbbell shaped products.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH.

Applications for LAMP have been further extended to include detection of RNA molecules by addition of Reverse Transcriptase enzyme (RT). By including RNA detection, the types of targets for which LAMP can be applied are also expanded and add the ability to additionally target RNA based viruses, important regulatory non-coding RNA (sRNA, miRNA), and RNA molecules that have been associated with particular disease or physiological states. The ability to detect RNA also has the potential to increase assay sensitivity, for instance in choosing highly expressed, stable, and/or abundant messenger RNA (mRNA) or ribosomal RNA (rRNA) targets. This preliminary phase of amplification involves the reverse transcription of RNA molecules to complementary DNA (cDNA). The cDNA then serves as template for the strand displacing DNA polymerase. Use of a thermostable RT enzyme (i.e., NEB RTx) enables the reaction to be completed at a single temperature and in a one step, single mix reaction.

A "target sequence," as used herein, means a nucleic acid sequence of Neisseria gonorrhoeae, or complement thereof, that is amplified, detected, or both amplified and detected using one or more of the polynucleotides herein provided. Additionally, while the term target sequence sometimes refers to a double stranded nucleic acid sequence, those skilled in the art will recognize that the target sequence can also be single stranded, e.g., RNA. A target sequence may be selected that is more or less specific for a particular organism. For example, the target sequence may be specific to an entire genus, to more than one genus, to a species or subspecies, serogroup, auxotype, serotype, strain, isolate or other subset of organisms.

The speed, specificity and sensitivity of the primers/probe compositions and method described herein result from several aspects. Exemplary primers for use in the compositions and methods according to the present invention include those provided in Table 1.

TABLE 1

Primer Sequences

| Sequence ID | Sequence (5' to 3') |
|---|---|
| SEQ ID NO: 1 | GAGCTACGAGCTGCCTGA |
| SEQ ID NO: 2 | TCTGCATCCTGTCGGCAA |
| SEQ ID NO: 3 | CCAGGAAGGAAGGCTGGAAGAGTCGGCCAGGTCATCACCAT |
| SEQ ID NO: 4 | CTGTGGCATCCACGAAACTACCTTCTGTGTTGGCGTACAGGTCT |
| SEQ ID NO: 5 | CGGAACCGCTCATTGCCA |
| SEQ ID NO: 6 | TCATGAAGTGTGACGTGGACATC |
| SEQ ID NO: 7 | AAGAGATGGCCACGGCTG |
| SEQ ID NO: 8 | ATGAAGTGTGACGTGGACATG |
| SEQ ID NO: 9 | GCGGAACCGCTCATTGCCAAGCTCCTCCCTGGAGAAGA |
| SEQ ID NO: 10 | ACTCTTCCAGCCTTCCTTCCTGGATGGAGTTGAAGGTAGTTTCGTG |
| SEQ ID NO: 11 | GTGATGACCTGGCCGTCAG |
| SEQ ID NO: 12 | GCATGGAGTCCTGTGGCATC |
| SEQ ID NO: 13 | CAGGATGCAGAAGGAGAT |
| SEQ ID NO: 14 | GTGTAACGCAACTAAGTCAT |
| SEQ ID NO: 15 | CCACACGGAGTACTTGCGCCAGCACAATGAAGATCAA |
| SEQ ID NO: 16 | CCAGCAGATGTGGATCAGCCTAGAAGCATTTGCGGTG |
| SEQ ID NO: 17 | CTCAGGAGGAGCAATGATC |
| SEQ ID NO: 18 | GACGAGT |
| SEQ ID NO: 19 | ACCCAGATCATGTTTGAGA |
| SEQ ID NO: 20 | ATCTCTTGCTCGAAGTCC |
| SEQ ID NO: 21 | CATCACGATGCCAGTGGTACCATGTACGTTGCTATCCAG |
| SEQ ID NO: 22 | CATGAAGATCCTCACCGAGCCTCCTTAATGTCACGCAC |
| SEQ ID NO: 23 | CAGAGGCGTACAGGGATA |
| SEQ ID NO: 24 | CTACAGCTTCACCACCAC |
| SEQ ID NO: 25 | ATCCACGAAACTACCTTCA |
| SEQ ID NO: 26 | GATCCACACGGAGTACTT |
| SEQ ID NO: 27 | CCAGACAGCACTGTGTTGGCCATCATGAAGTGTGACG |
| SEQ ID NO: 28 | ACAGGATGCAGAAGGAGATCACAGGAGGAGCAATGATCT |
| SEQ ID NO: 29 | CAGGTCTTTGCGGATGTC |
| SEQ ID NO: 30 | CACCCAGCACAATGAAGAT |
| SEQ ID NO: 31 | GTGATGGTGGGCATGG |
| SEQ ID NO: 32 | TGGGTCATCTTCTCGC |
| SEQ ID NO: 33 | GTGACGATGCCGTGCTCTCAGAAGGATTCCTATGTGG |
| SEQ ID NO: 34 | AACTGGGACGACATGGAGACACACGCAGCTCATTG |
| SEQ ID NO: 35 | GGTGAGGATGCCTCTC |

TABLE 1-continued

Primer Sequences

| Sequence ID | Sequence (5' to 3') |
|---|---|
| SEQ ID NO: 36 | TCTGGCACCACACCTT |
| SEQ ID NO: 37 | CTTCCCCTCCATCGTG |
| SEQ ID NO: 38 | CACACGCAGCTCATTG |
| SEQ ID NO: 39 | TGAGGATGCCTCTCTTGCTCGTGATGGTGGGCAT |
| SEQ ID NO: 40 | CCATCGAGCACGGCATCGAAGGTGTGGTGCCA |
| SEQ ID NO: 41 | CACATAGGAATCCTTCTGACC |
| SEQ ID NO: 42 | CTGGGACGACATGGAGA |
| SEQ ID NO: 43 | CGTGATGGTGGGCAT |
| SEQ ID NO: 44 | GGGTACTTCAGGGTGAGGATCAGAAGGATTCCTATGTGG |
| SEQ ID NO: 45 | GAGCACGGCATCGTCACGAAGGTGTGGTGCCA |
| SEQ Id NO: 46 | TGCCTCTCTTGCTCTGG |
| SEQ ID NO: 47 | GAGAGGCATCCTCACC |
| SEQ ID NO: 48 | GTAGATGGGCACAGTGT |
| SEQ ID NO: 49 | CCACACGCAGCTCATTGTAATCGAGCACGGCATC |
| SEQ ID NO: 50 | TGCTATCCAGGCTGTGCTAAGTCCATCACGATGCC |
| SEQ ID NO: 51 | AAGGTGTGGTGCCAGA |
| SEQ ID NO: 52 | CTCTGGCCGTACCACT |
| SEQ ID NO: 53 | ATCGAGCACGGCATC |
| SEQ ID NO: 54 | CCACACGCAGCTCATTGTGGGACGACATGGAGAAA |
| SEQ ID NO: 55 | TCAGAAGGATTCCTATGTGG |
| SEQ ID NO: 56 | TCTCCATGTCGTCCCAGTTGAGAGGCATCCTCACC |
| SEQ ID NO: 57 | TGACGATGCCGTGCT |
| SEQ ID NO: 58 | ACCGCGAGAAGATGAC |
| SEQ ID NO: 59 | GACGCAGGATGGCAT |
| SEQ ID NO: 60 | CCAGAGGCGTACAGGGATTCATGTTTGAGACCTTCAAC |
| SEQ ID NO: 61 | CGTACCACTGGCATCGTGGTAGATGGGCACAGTGT |
| SEQ ID NO: 62 | CACAGCCTGGATAGCAAC |
| SEQ ID NO: 63 | ATGGACTCCGGTGACG |
| SEQ ID NO: 64 | TCGCCTTTGCCGATC |
| SEQ ID NO: 65 | GGAATCCTTCTGACCCAT |
| SEQ ID NO: 66 | CATGCCGGAGCCGTTGCGCCAGCTCACCATG |
| SEQ ID NO: 67 | TTCGCGGGCGACGATCATCACGCCCTGGTG |
| SEQ ID NO: 68 | GCGCGGCGATATCATC |
| SEQ ID NO: 69 | GTCTTCCCCTCCATCGT |
| SEQ ID NO: 70 | CGAGCACAGAGCCTC |
| SEQ ID NO: 71 | CGAGCGCGGCGATATCGCCTTTGCCGATCCG |
| SEQ ID NO: 72 | CATCCATGGTGAGCTGG |
| SEQ ID NO: 73 | GATGCCGTGCTCGAT |

TABLE 1-continued

Primer Sequences

| Sequence ID | Sequence (5' to 3') |
|---|---|
| SEQ ID NO: 74 | CCGGCCTTGCACATGCCGCCAGCTCACCATG |
| SEQ ID NO: 75 | CGTGATGGTGGGCATGGGGTGAGGATGCCTCTC |
| SEQ ID NO: 76 | TGTCGACGACGAGCG |
| SEQ ID NO: 77 | GTCAGAAGGATTCCTATGTGG |
| SEQ ID NO: 78 | CGCCAGCTCACCATG |
| SEQ ID NO: 79 | CATCACGCCCTGGTGCTCGTCGTCGACAACG |
| SEQ ID NO: 80 | GGTCAGAAGGATTCCTATGTGGGGTGAGGATGCCTCTC |
| SEQ ID NO: 81 | CCGGCCTTGCACATG |
| SEQ ID NO: 82 | CGAGGCCCAGAGCAA |
| SEQ ID NO: 83 | ATGAGCTGCGTGTGGCTCCC |
| SEQ ID NO: 84 | GGGCATACCCCTCGTAGATGGG |
| SEQ ID NO: 85 | AGCACAGCCTGGATAGCAACGTACACCAAGGCCAACCGCGAGAAG |
| SEQ ID NO: 86 | ATCCCTGTACGCCTCTGGCCGTACCAGTGTGGGTGACCCCGTCA |
| SEQ ID NO: 87 | TGGCTGGGGTGTTGAAGGTCTCA |
| SEQ ID NO: 88 | CACTGGCATCGTGATGGACTCCG |
| SEQ ID NO: 89 | CTGGACTTCGAGCAAGAGATGGC |
| SEQ ID NO: 90 | TGTTGGCGTACAGGTCTTTGCG |
| SEQ ID NO: 91 | AAGAGTGCCTCAGGGCAGCGGAAGGAGAAGAGCTACGAGCTGCCT |
| SEQ ID NO: 92 | CCAGCCTTCCTTCCTGGGCATGGACCACGTCACACTTCATGATGGAGTT |
| SEQ ID NO: 93 | GCTCATTGCCAATGGTGATGACCTG |
| SEQ ID NO: 94 | CCTGTGGCATCCACGAAACTACCTT |
| SEQ ID NO: 95 | ACGGCTGCTTCCAGCTCCTC |
| SEQ ID NO: 96 | GACAGCACTGTGTTGGCGTACA |
| SEQ ID NO: 97 | AAGAGTGCCTCAGGGCAGCGGAAAGCTACGAGCTGCCTGACGG |
| SEQ ID NO: 98 | AGCCTTCCTTCCTGGGCATGGAGTCCCACGTCACACTTCATGATGGAGT |
| SEQ ID NO: 99 | TGTGGCATCCACGAAACTACCTTCA |
| SEQ ID NO: 100 | GCGGATGTCCACGTCACACTTC |
| SEQ ID NO: 101 | CCAATGGTGATGACCTGGCCGTCAGACGGCTGCTTCCAGCTCCTC |
| SEQ ID NO: 102 | ATGAGCGGTTCCGCTGCCCTGATCGTGGATGCCACAGGACTCC |
| SEQ ID NO: 103 | GCAGCTCGTAGCTCTTCTCCAGG |
| SEQ ID NO: 104 | GCACTCTTCCAGCCTTCCTTCCTG |
| SEQ ID NO: 105 | ATGAGCGGTTCCGCTGCCCTGAGATGCCACAGGACTCCATGCC |
| SEQ ID NO: 106 | CCAGAGGCGTACAGGGATCCAGATCATGTTTGAGACC |
| SEQ ID NO: 107 | CCAACCGCGAGAAGAT |
| SEQ ID NO: 108 | AGAGGCGTACAGGGATAGCACCCAGATCATGTTTGAGA |
| SEQ ID NO: 109 | ATAGCAACGTACATGGCTG |
| SEQ ID NO: 110 | AGAGGCGTACAGGGATAGCGACCCAGATCATGTTTGAG |
| SEQ ID NO: 111 | CCAACCGCGAGAAGA |

TABLE 1-continued

Primer Sequences

| Sequence ID | Sequence (5' to 3') |
| --- | --- |
| SEQ ID NO 112 | GAGGCGTACAGGGATAGCATGACCCAGATCATGTTTGA |
| SEQ ID NO: 113 | TTCTACAATGAGCTGCGTGT |
| SEQ ID NO: 114 | CGGAGTCCATCACGATGC |
| SEQ ID NO: 115 | AAGGTCTCAAACATGATCTGGGTCACGTGCTGCTGACCGAG |
| SEQ ID NO: 116 | CCAGCCATGTACGTTGCTATCCAAGTGGTACGGCCAGAGG |
| SEQ ID NO: 117 | TCGCGGTTGGCCTTGG |
| SEQ ID NO: 118 | GGCTGTGCTATCCCTGTACG |
| SEQ ID NO: 119 | AATCTGGCACCACACCTTC |
| SEQ ID NO: 120 | AGGCGTACAGGGATAGCA |
| SEQ ID NO: 121 | TTGGCCTTGGGGTTCAGGGGAGCTGCGTGTGGCTC |
| SEQ ID NO: 122 | GCGAGAAGATGACCCAGATCATGTGCCTGGATAGCAACGTACAT |
| SEQ ID NO: 123 | GCCTCGGTCAGCAGCA |
| SEQ ID NO: 124 | AGACCTTCAACACCCCAGC |
| SEQ ID NO: 125 | GCACGGCATCGTCACC |
| SEQ ID NO: 126 | GCCTGGATAGCAACGTACAT |
| SEQ ID NO: 127 | AGCCACACGCAGCTCATTGTAACTGGGACGACATGGAGA |
| SEQ ID NO: 128 | TGAACCCCAAGGCCAACCGCTGGGGTGTTGAAGGTCTC |
| SEQ ID NO: 129 | AGAAGGTGTGGTGCCAGATT |
| SEQ ID NO: 130 | CGAGAAGATGACCCAGATCATGT |
| SEQ ID NO: 131 | ACGGCATCGTCACCAAC |
| SEQ ID NO: 132 | TGCTCCTCGGGAGCCACAGACATGGAGAAAATCTGGCAC |
| SEQ ID NO: 133 | TGAACCCCAAGGCCAACCGTGGGGTGTTGAAGGTCTCA |
| SEQ ID NO: 134 | GCAGCTCATTGTAGAAGGTGTG |

Detection of the LAMP amplified products can be achieved via a variety of methods. In a preferred embodiment, detection of product is conducted by adding a fluorescently-labeled probe to the primer mix. The term used herein "probe" refers to a single-stranded nucleic acid molecule comprising a portion or portions that are complementary, or substantially complementary, to a target sequence. In certain implementations, the fluorescently-labeled probe is a molecular beacon.

As used herein, "molecular beacon" refers to a single stranded hairpin-shaped oligonucleotide probe designed to report the presence of specific nucleic acids in a solution. A molecular beacon consists of four components; a stem, hairpin loop, end labelled fluorophore and opposite end-labelled quencher (Tyagi et al., (1998) Nature Biotechnology 16:49-53). When the hairpin-like beacon is not bound to a target, the fluorophore and quencher lie close together and fluorescence is suppressed. In the presence of a complementary target nucleotide sequence, the stem of the beacon opens to hybridize to the target. This separates the fluorophore and quencher, allowing the fluorophore to fluoresce. Alternatively, molecular beacons also include fluorophores that emit in the proximity of an end-labelled donor. "Wavelength-shifting Molecular Beacons" incorporate an additional harvester fluorophore enabling the fluorophore to emit more strongly. Current reviews of molecular beacons include Wang et al., 2009, Angew Chem Int Ed Engl, 48(5):856-870; Cissell et al., 2009, Anal Bioanal Chem 393(1):125-35; Li et al., 2008, Biochem Biophys Res Comm 373(4):457-61; and Cady, 2009, Methods Mol Biol 554:367-79.

In one implementation, the molecular beacon comprises a fluorophore, a quencher, and a polynucleotide, wherein the polynucleotide comprises a sequence selected from the group consisting of nucleotides 6-33 of SEQ ID NO: 135, nucleotides 6-30 of SEQ ID NO: 136, nucleotides 7-27 of SEQ ID NO: 137, nucleotides 7-26 of SEQ ID NO: 138, nucleotides 1-26 of SEQ ID NO: 139, nucleotides 7-26 of SEQ ID NO: 140, nucleotides 7-30 of SEQ ID NO: 141, nucleotides 6-30 of SEQ ID NO: 142, nucleotides 8-32 of SEQ ID NO: 143, nucleotides 8-30 of SEQ ID NO: 144, nucleotides 6-31 of SEQ ID NO: 145, nucleotides 8-30 of SEQ ID NO: 146, 8-22 of SEQ ID NO: 147, nucleotides 8-24 of SEQ ID NO: 148, nucleotides 7-27 of SEQ ID NO:

149, nucleotides 8-21 of SEQ ID NO: 150, nucleotides 8-32 of SEQ ID NO: 151, nucleotides 1-24 of SEQ ID NO: 152, nucleotides 4-24 of SEQ ID NO: 153, nucleotides 1-23 of SEQ ID NO: 154, nucleotides 8-26 of SEQ ID NO: 155, nucleotides 7-29 of SEQ ID NO: 156, nucleotides 8-28 of SEQ ID NO: 157, nucleotides 8-29 of SEQ ID NO: 158, nucleotides 7-25 of SEQ ID NO: 159, nucleotides 8-22 of SEQ ID NO: 160, nucleotides 6-22 of SEQ ID NO: 161, nucleotides 3-22 of SEQ ID NO: 162, nucleotides 8-28 of SEQ ID NO: 163, nucleotides 3-28 of SEQ ID NO: 164, nucleotides 5-25 of SEQ ID NO: 165, nucleotides 5-26 of SEQ ID NO: 166, nucleotides 5-20 of SEQ ID NO: 167, nucleotides 4-22 of SEQ ID NO: 168, nucleotides 7-22 of SEQ ID NO: 169, nucleotides 3-22 of SEQ ID NO: 170, nucleotides 7-28 of SEQ ID NO: 171, nucleotides 6-27 of SEQ ID NO: 172, nucleotides 7-29 of SEQ ID NO: 173, nucleotides 5-27 of SEQ ID NO: 174, nucleotides 7-29 of SEQ ID NO: 175, nucleotides 6-28 of SEQ ID NO: 176, nucleotides 4-23 of SEQ ID NO: 177, nucleotides 4-34 of SEQ ID NO: 178, nucleotides 3-27 of SEQ ID NO: 179, nucleotides 2-27 of SEQ ID NO: 180, nucleotides 5-33 of SEQ ID NO: 181, nucleotides 3-30 of SEQ ID NO: 182, nucleotides 9-34 of SEQ ID NO: 183, and nucleotides 8-28 of SEQ ID NO: 184. In one embodiment, the polynucleotide comprises a sequence selected from the group consisting of SEQ ID NO: 135 through SEQ ID NO: 184. In another embodiment, the polynucleotide consists of a sequence selected from the group consisting of SEQ ID NO: 135 through SEQ ID NO: 184.

The molecular beacon is preferably used in a composition also comprising a set of sequence-specific LAMP primers. In one implementation, the molecular beacon comprises a sequence selected from the group consisting of nucleotides 6-33 of SEQ ID NO: 135, nucleotides 6-30 of SEQ ID NO: 136, nucleotides 7-27 of SEQ ID NO: 137, nucleotides 7-26 of SEQ ID NO: 138, nucleotides 1-26 of SEQ ID NO: 139, nucleotides 7-26 of SEQ ID NO: 140, nucleotides 7-30 of SEQ ID NO: 141, nucleotides 6-30 of SEQ ID NO: 142, nucleotides 8-32 of SEQ ID NO: 143, nucleotides 8-30 of SEQ ID NO: 144, nucleotides 6-31 of SEQ ID NO: 145, nucleotides 8-30 of SEQ ID NO: 146, 8-22 of SEQ ID NO: 147, nucleotides 8-24 of SEQ ID NO: 148, nucleotides 7-27 of SEQ ID NO: 149, nucleotides 8-21 of SEQ ID NO: 150, nucleotides 8-32 of SEQ ID NO: 151, nucleotides 1-24 of SEQ ID NO: 152, nucleotides 4-24 of SEQ ID NO: 153, nucleotides 1-23 of SEQ ID NO: 154, nucleotides 8-26 of SEQ ID NO: 155, nucleotides 7-29 of SEQ ID NO: 156, nucleotides 8-28 of SEQ ID NO: 157, nucleotides 8-29 of SEQ ID NO: 158, nucleotides 7-25 of SEQ ID NO: 159, nucleotides 8-22 of SEQ ID NO: 160, nucleotides 6-22 of SEQ ID NO: 161, nucleotides 3-22 of SEQ ID NO: 162, nucleotides 8-28 of SEQ ID NO: 163, nucleotides 3-28 of SEQ ID NO: 164, nucleotides 5-25 of SEQ ID NO: 165, nucleotides 5-26 of SEQ ID NO: 166, nucleotides 5-20 of SEQ ID NO: 167, nucleotides 4-22 of SEQ ID NO: 168, nucleotides 7-22 of SEQ ID NO: 169, nucleotides 3-22 of SEQ ID NO: 170, nucleotides 7-28 of SEQ ID NO: 171, nucleotides 6-27 of SEQ ID NO: 172, nucleotides 7-29 of SEQ ID NO: 173, nucleotides 5-27 of SEQ ID NO: 174, nucleotides 7-29 of SEQ ID NO: 175, nucleotides 6-28 of SEQ ID NO: 176, nucleotides 4-23 of SEQ ID NO: 177, nucleotides 4-34 of SEQ ID NO: 178, nucleotides 3-27 of SEQ ID NO: 179, nucleotides 2-27 of SEQ ID NO: 180, nucleotides 5-33 of SEQ ID NO: 181, nucleotides 3-30 of SEQ ID NO: 182, nucleotides 9-34 of SEQ ID NO: 183, and nucleotides 8-28 of SEQ ID NO: 184. In such an implementation, the molecular beacon can comprise a sequence selected from the group consisting of SEQ ID NO: 135 through SEQ ID NO: 184. More preferably, polynucleotide sequence of the molecular beacon consists of a sequence selected from the group consisting of SEQ ID NO: 135 through SEQ ID NO: 184. In a particularly preferred implementation, the polynucleotide sequence of the molecular beacon is SEQ ID NO: 184.

When included in a composition comprising a set of polynucleotides selected from the group consisting of Sets-9-12, Set-17, and Sets-22-29, the molecular beacon preferably comprises a sequence selected from the group consisting of nucleotides 8-22 of SEQ ID NO: 147, nucleotides 8-24 of SEQ ID NO: 148, nucleotides 7-27 of SEQ ID NO: 149, nucleotides 8-21 of SEQ ID NO: 150, nucleotides 8-26 of SEQ ID NO: 155, nucleotides 7-29 of SEQ ID NO: 156, nucleotides 5-25 of SEQ ID NO: 165, nucleotides 5-26 of SEQ ID NO: 166, nucleotides 5-20 of SEQ ID NO: 167, nucleotides 4-22 of SEQ ID NO: 168, nucleotides 7-22 of SEQ ID NO: 169, nucleotides 7-28 of SEQ ID NO: 171, nucleotides 6-27 of SEQ ID NO: 172, nucleotides 7-29 of SEQ ID NO: 173, nucleotides 5-27 of SEQ ID NO: 174, nucleotides 7-29 of SEQ ID NO: 175, nucleotides 6-28 of SEQ ID NO: 176, nucleotides 9-46 of SEQ ID NO: 183, and nucleotides 8-40 of SEQ ID NO: 184. More particularly, the molecular beacon can comprise a sequence selected from the group consisting of SEQ ID NO: 147, SEQ ID NO: 148, SEQ ID NO: 149, SEQ ID NO: 150, SEQ ID NO: 155, SEQ ID NO: 156, SEQ ID NO: 165, SEQ ID NO: 166, SEQ ID NO: 167, SEQ ID NO: 168, SEQ ID NO: 169, SEQ ID NO: 171, SEQ ID NO: 172, SEQ ID NO: 173, SEQ ID NO: 174, SEQ ID NO: 175, SEQ ID NO: 176, SEQ ID NO: 183, and SEQ ID NO: 184. In certain implementations, the sequence of the molecular beacon is selected from the group consisting of SEQ ID NO: 147, SEQ ID NO: 148, SEQ ID NO: 149, SEQ ID NO: 150, SEQ ID NO: 155, SEQ ID NO: 156, SEQ ID NO: 165, SEQ ID NO: 166, SEQ ID NO: 167, SEQ ID NO: 168, SEQ ID NO: 169, SEQ ID NO: 171, SEQ ID NO: 172, SEQ ID NO: 173, SEQ ID NO: 174, SEQ ID NO: 175, SEQ ID NO: 176, SEQ ID NO: 183, and SEQ ID NO: 184.

When included in a composition comprising a set of polynucleotides selected from the group consisting of Sets 9-11, Set-17, and Sets 23-29, the molecular beacon preferably comprises a sequence selected from the group consisting of nucleotides 1-24 of SEQ ID NO: 152, nucleotides 4-24 of SEQ ID NO: 153, and nucleotides 1-23 of SEQ ID NO: 154. In certain implementations, the molecular beacon can comprise a sequence selected from the group consisting of SEQ ID NO: 152, SEQ ID NO: 153, and SEQ ID NO:154. In some embodiments, the sequence of the molecular beacon is selected from the group consisting of SEQ ID NO: 152, SEQ ID NO: 153, and SEQ ID NO:154.

When used in combination with a set of polynucleotides selected from the group consisting of Set-4, Sets 9-12, Set-17, and Sets 22-26, the molecular beacon preferably comprises a sequence selected from the group consisting of 8-30 of SEQ ID NO: 144, nucleotides 6-31 of SEQ ID NO: 145, and nucleotides 8-30 of SEQ ID NO: 146. In some embodiments, the molecular beacon can comprise a sequence selected from the group consisting of SEQ ID NO: 144, SEQ ID NO: 145, and SEQ ID NO: 146. In other embodiments, the sequence of the molecular beacon is selected from the group consisting of SEQ ID NO: 144, SEQ ID NO: 145, and SEQ ID NO: 146.

When included in a composition comprising a set of polynucleotides selected from the group consisting of Set-5, Set-12, Set-17, and Sets 22-25, the molecular beacon preferably comprises nucleotides 3-22 of SEQ ID NO: 170. In some implementations, the molecular beacon comprises SEQ ID NO: 170. In other embodiments, the sequence of the molecular beacon is SEQ ID NO: 170.

When used in combination with a set of polynucleotides selected from the group consisting of Sets 6-8, Set-15, and Set-16, the molecular beacon preferably comprises a sequence selected from the group consisting of nucleotides 2-27 of SEQ ID NO: 180 and nucleotides 3-30 of SEQ ID NO: 182. In such an embodiment, the molecular beacon can comprise a sequence selected from the group consisting of SEQ ID NO: 180 and SEQ ID NO: 182. In another embodiment, the sequence of the molecular beacon is SEQ ID NO: 180 or SEQ ID NO: 182.

When included in a composition comprising a set of polynucleotides selected from the group consisting of Sets 6-11, Set-28, and Set-29, the molecular beacon preferably comprises a sequence selected from the group consisting of nucleotides 4-34 of SEQ ID NO: 178 and nucleotides 5-33 of SEQ ID NO: 181. In some embodiments, the molecular beacon can comprise a sequence selected from the group consisting of SEQ ID NO: 178 and SEQ ID NO: 181. In other embodiments, the sequence of the molecular beacon is SEQ ID NO: 178 or SEQ ID NO: 181.

When used in combination with a set of polynucleotides selected from the group consisting of Sets 6-9 and Set-11, the molecular beacon preferably comprises nucleotides 3-27 of SEQ ID NO: 179. In some implementations, the molecular beacon comprises SEQ ID NO: 179. In other embodiments, the sequence of the molecular beacon is SEQ ID NO: 179.

When included in a composition comprising a set of polynucleotides selected from the group consisting of Sets 6-9, Set-11, and Set-28, the molecular beacon preferably comprises nucleotides 4-23 of SEQ ID NO: 177. In some embodiments, the molecular beacon comprises SEQ ID NO: 177. In other embodiments, the sequence of the molecular beacon is SEQ ID NO: 177.

When used in combination with a set of polynucleotides selected from the group consisting of Sets 13-15, the molecular beacon preferably comprises a sequence selected from the group consisting of nucleotides 7-25 of SEQ ID NO: 159 and nucleotides 8-22 of SEQ ID NO: 160. In such an embodiment, the molecular beacon can comprise a sequence selected from the group consisting of SEQ ID NO: 159 and SEQ ID NO: 160. In other embodiments, the sequence of the molecular beacon is SEQ ID NO: 159 or SEQ ID NO: 160.

When included in a composition comprising a set of polynucleotides selected from the group consisting of Sets 13-16, the molecular beacon preferably comprises a sequence selected from the group consisting of nucleotides 8-28 of SEQ ID NO: 157, nucleotides 8-29 of SEQ ID NO: 158, nucleotides 6-22 of SEQ ID NO: 161, and nucleotides 3-22 of SEQ ID NO: 162. More particularly, the molecular beacon can comprise a sequence selected from the group consisting of SEQ ID NO: 157, SEQ ID NO: 158, SEQ ID NO: 161, and SEQ ID NO: 162. In certain implementations, the sequence of the molecular beacon is selected from the group consisting of SEQ ID NO: 157, SEQ ID NO: 158, SEQ ID NO: 161, and SEQ ID NO: 162.

When used in combination with a set of polynucleotides consisting of Set-3, the molecular beacon preferably comprises a sequence selected from the group consisting nucleotides 7-27 of SEQ ID NO: 137, nucleotides 7-26 of SEQ ID NO: 138, nucleotides 1-26 of SEQ ID NO: 139, nucleotides 7-26 of SEQ ID NO: 140, nucleotides 7-30 of SEQ ID NO: 141, nucleotides 6-30 of SEQ ID NO: 142, nucleotides 8-32 of SEQ ID NO: 151, and nucleotides 4-24 of SEQ ID NO: 153. In certain implementations, the molecular beacon can comprise a sequence selected from the group consisting of SEQ ID NO: 137, SEQ ID NO: 138, SEQ ID NO: 139, SEQ ID NO: 140, SEQ ID NO: 141, SEQ ID NO: 142, SEQ ID NO: 151, and SEQ ID NO: 153. In some embodiments, the sequence of the molecular beacon is selected from the group consisting of SEQ ID NO: 137, SEQ ID NO: 138, SEQ ID NO: 139, SEQ ID NO: 140, SEQ ID NO: 141, SEQ ID NO: 142, SEQ ID NO: 151, and SEQ ID NO: 153.

When included in a composition comprising a set of polynucleotides selected from the group consisting of Set-1, Set-2, and Sets 18-20, the molecular beacon preferably comprises a sequence selected from the group consisting of nucleotides 8-28 of SEQ ID NO: 163 and nucleotides 3-28 of SEQ ID NO: 164. In certain implementations, the molecular beacon can comprise a sequence selected from the group consisting of SEQ ID NO: 163 and SEQ ID NO: 164. In some embodiments, the sequence of the molecular beacon is SEQ ID NO: 163 or SEQ ID NO: 164.

When included in a composition comprising a set of polynucleotides selected from the group consisting of Set-1, Set-2 and Sets 18-21, the molecular beacon preferably comprises a sequence selected from the group consisting of nucleotides 6-33 of SEQ ID NO: 135 and nucleotides 6-30 of SEQ ID NO: 136. In some implementations, the molecular beacon can comprise a sequence selected from the group consisting of SEQ ID NO: 135 and SEQ ID NO: 136. In other embodiments, the sequence of the molecular beacon is SEQ ID NO: 135 or SEQ ID NO: 136. The polynucleotides having the sequences described above can include one or more non-natural nucleosides or linkages, such as peptide nucleic acid (PNA), morpholino, locked nucleic acid (LNA), glycol nucleic acid (GNA) and threose nucleic acid (TNA), among others. In some embodiments, the polynucleotide of the molecular beacon comprises one to six locked nucleic acids. In a preferred embodiment, the polynucleotide of the molecular beacon comprises three or four locked nucleic acids.

The term "label" as used herein means a molecule or moiety having a property or characteristic which is capable of detection and, optionally, of quantitation. A label can be directly detectable, as with, for example (and without limitation), radioisotopes, fluorophores, chemiluminophores, enzymes, colloidal particles, fluorescent microparticles and the like; or a label may be indirectly detectable, as with, for example, specific binding members. It will be understood that directly detectable labels may require additional components such as, for example, substrates, triggering reagents, quenching moieties, light, and the like to enable detection and/or quantitation of the label. When indirectly detectable labels are used, they are typically used in combination with a "conjugate". A conjugate is typically a specific binding member that has been attached or coupled to a directly detectable label. Coupling chemistries for synthesizing a conjugate are well known in the art and can include, for example, any chemical means and/or physical means that does not destroy the specific binding property of the specific binding member or the detectable property of the label. As used herein, "specific binding member" means a member of a binding pair, i.e., two different molecules where one of the molecules through, for example, chemical or physical means specifically binds to the other molecule. In addition to antigen and antibody specific binding pairs, other specific binding pairs include, but are not intended to be limited to, avidin and biotin; haptens and antibodies specific for haptens; complementary nucleotide sequences; enzyme cofactors or substrates and enzymes; and the like.

The molecular beacon can be composed of nucleic acid only such as DNA or RNA, or it can be composed of a peptide nucleic acid (PNA) conjugate. The fluorophore can be any fluorescent organic dye or a single quantum dot. The quenching moiety desirably quenches the luminescence of the fluorophore. Any suitable quenching moiety that quenches the luminescence of the fluorophore can be used. A fluorophore can be any fluorescent marker/dye known in the art. Examples of suitable fluorescent markers include, but are not limited to, Fam, Hex, Tet, Joe, Rox, Tamra, Max, Edans, Cy dyes such as Cy5, Fluorescein, Coumarin, Eosine, Rhodamine, Bodipy, Alexa, Cascade Blue, Yakima Yellow, Lucifer Yellow, Texas Red, and the family of ATTO dyes. A quencher can be any quencher known in the art. Examples of quenchers include, but are not limited to, Dabcyl, Dark Quencher, Eclipse Dark Quencher, ElleQuencher, Tamra, BHQ and QSY (all of them are Trade-Marks). The skilled person would know which combinations of dye/quencher are suitable when designing a probe. In an exemplary embodiment, fluorescein (FAM) is used in conjunction with Blackhole Quencher™ (BHQ™) (Novato, Calif.). Binding of the molecular beacon to amplified product can then be directly, visually assessed. Alternatively, the fluorescence level can be measured by spectroscopy in order to improve sensitivity.

A variety of commercial suppliers produce standard and custom molecular beacons, including Abingdon Health (UK; (www) abingdonhealth.com), Attostar (US, MN; (www) attostar.com), Biolegio (NLD; (www) biolegio.com), Biomers.net (DEU; (www) biomers.net), Biosearch Technologies (US, CA; (www) biosearchtech.com), Eurogentec (BEL; (www) eurogentec.com), Gene Link (US, NY; (www) genelink.com) Integrated DNA Technologies (US, IA; (www) idtdna.com), Isogen Life Science (NLD; (www) isogenlifescience.com), Midland Certified Reagent (US, TX; (www) oligos.com), Eurofins (DEU; (www) eurofinsgenomics.eu), Sigma-Aldrich (US, TX; (www) sigmaaldrich.com), Thermo Scientific (US, MA; (www) thermoscientific.com), TIB MOLBIOL (DEU; (www) tibmolbiol.de), TriLink Bio Technologies (US, CA; (www) trilinkbiotech.com). A variety of kits, which utilize molecular beacons are also commercially available, such as the Sentinel™ Molecular Beacon Allelic Discrimination Kits from Stratagene (La Jolla, Calif.) and various kits from Eurogentec SA (Belgium, eurogentec.com) and Isogen Bioscience BV (The Netherlands, isogen.com).

The oligonucleotide probes and primers of the invention are optionally prepared using essentially any technique known in the art. In certain embodiments, for example, the oligonucleotide probes and primers described herein are synthesized chemically using essentially any nucleic acid synthesis method, including, e.g., according to the solid phase phosphoramidite triester method described by Beaucage and Caruthers (1981), Tetrahedron Letts. 22(20): 1859-1862, which is incorporated by reference, or another synthesis technique known in the art, e.g., using an automated synthesizer, as described in Needham-VanDevanter et al. (1984) Nucleic Acids Res. 12:6159-6168, which is incorporated by reference. A wide variety of equipment is commercially available for automated oligonucleotide synthesis. Multi-nucleotide synthesis approaches (e.g., tri-nucleotide synthesis, etc.) are also optionally utilized. Moreover, the primer nucleic acids described herein optionally include various modifications. To further illustrate, primers are also optionally modified to improve the specificity of amplification reactions as described in, e.g., U.S. Pat. No. 6,001,611, issued Dec. 14, 1999, which is incorporated by reference. Primers and probes can also be synthesized with various other modifications as described herein or as otherwise known in the art.

In addition, essentially any nucleic acid (and virtually any labeled nucleic acid, whether standard or non-standard) can be custom or standard ordered from any of a variety of commercial sources, such as Integrated DNA Technologies, the Midland Certified Reagent Company, Eurofins, Biosearch Technologies, Sigma Aldrich and many others.

The term "test sample" as used herein, means a sample taken from an organism or biological fluid that is suspected of containing or potentially contains a target sequence. The test sample can be taken from any biological source, such as for example, tissue, blood, saliva, sputa, mucus, sweat, urine, urethral swabs, cervical swabs, vaginal swabs, urogenital or anal swabs, conjunctival swabs, ocular lens fluid, cerebral spinal fluid, milk, ascites fluid, synovial fluid, peritoneal fluid, amniotic fluid, fermentation broths, cell cultures, chemical reaction mixtures and the like. The test sample can be used (i) directly as obtained from the source or (ii) following a pre-treatment to modify the character of the sample. Thus, the test sample can be pre-treated prior to use by, for example, preparing plasma or serum from blood, disrupting cells or viral particles, preparing liquids from solid materials, diluting viscous fluids, filtering liquids, distilling liquids, concentrating liquids, inactivating interfering components, adding reagents, purifying nucleic acids, and the like.

Advantageously, the invention enables reliable rapid detection of β-actin in a clinical sample, such as a urine sample.

To further illustrate, prior to analyzing the target nucleic acids described herein, those nucleic acids may be purified or isolated from samples that typically include complex mixtures of different components. Cells in collected samples are typically lysed to release the cell contents, including target nucleic acids. For example, a test sample suspected of containing a sexually transmitted infection (STI), including, but not limited to, Chlamydia trachomatis (CT), Neisseria gonorrhea (NG) and Trichomonas vaginalis (TV), can be lysed by contacting cells with various enzymes, chemicals, and/or lysed by other approaches known in the art, which degrade, e.g., bacterial cell walls. In some embodiments, nucleic acids are analyzed directly in the cell lysate. In other embodiments, nucleic acids are further purified or extracted from cell lysates prior to detection. Essentially any nucleic acid extraction methods can be used to purify nucleic acids in the samples utilized in the methods of the present invention. Exemplary techniques that can be used to purifying nucleic acids include, e.g., affinity chromatography, hybridization to probes immobilized on solid supports, liquid-liquid extraction (e.g., phenol-chloroform extraction, etc.), precipitation (e.g., using ethanol, etc.), extraction with filter paper, extraction with micelle-forming reagents (e.g., cetyl-trimethyl-ammonium-bromide, etc.), binding to immobilized intercalating dyes (e.g., ethidium bromide, acridine, etc.), adsorption to silica gel or diatomic earths, adsorption to magnetic glass particles or organo silane particles under chaotropic conditions, and/or the like. Sample processing is also described in, e.g., U.S. Pat. Nos. 5,155,018, 6,383,393, and 5,234,809, which are each incorporated by reference.

A test sample may optionally have been treated and/or purified according to any technique known by the skilled person, to improve the amplification efficiency and/or qualitative accuracy and/or quantitative accuracy. The sample may thus exclusively, or essentially, consist of nucleic acid(s), whether obtained by purification, isolation, or by chemical synthesis. Means are available to the skilled person, who would like to isolate or purify nucleic acids, such as DNA, from a test sample, for example to isolate or purify DNA from cervical scrapes (e.g., QIAamp-DNA Mini-Kit; Qiagen, Hilden, Germany).

Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Target Selection and Primer Probe Design

Primer/probe based detection assays were designed to utilize isothermal loop mediated amplification (LAMP) targeting RNA through the addition of a Reverse transcriptase (RT-LAMP) to the reaction. A molecular beacon probe with 5' fluorophore/3' quencher modifications (6-Carboxyfluorescein and Black Hole Quencher 1 was included to provide target-specific fluorescent detection. β-actin RT-LAMP primer sets (Table 1 and Table 2) were designed using a combination of software programs including Premier Biosoft's LAMP Designer, Beacon Designer, an in-house script and manual designs. Designed primer sets and beacons were further analyzed for specificity using BLAST against the human genome and the NCBI nucleotide database. Various primer sets and probes were designed and screened for reaction speed.

The inventive primer sets are summarized in Table 2, which include, at a minimum, a forward inner primer (FIP) and backward inner primer (BIP). Additionally, the primer sets typically also include at least two additional primers selected from the forward outer primer (F3), backward outer primer (B3), forward loop primer (LF) and backward loop primer (LB).

TABLE 2

| LAMP Primer Sets | | | | | | |
|---|---|---|---|---|---|---|
| Set | F3 | B3 | FIP | BIP | LF | LB |
| Set-1 | SEQ ID NO: 1 | SEQ ID NO: 2 | SEQ ID NO: 3 | SEQ ID NO: 4 | SEQ ID NO: 5 | SEQ ID NO: 6 |
| Set-2 | SEQ ID NO: 7 | SEQ ID NO: 8 | SEQ ID NO: 9 | SEQ ID NO: 10 | SEQ ID NO: 11 | SEQ ID NO: 12 |
| Set-3 | SEQ ID NO: 13 | SEQ ID NO: 14 | SEQ ID NO: 15 | SEQ ID NO: 16 | SEQ ID NO: 17 | SEQ ID NO: 18 |
| Set-4 | SEQ ID NO: 19 | SEQ ID NO: 20 | SEQ ID NO: 21 | SEQ ID NO: 22 | SEQ ID NO: 23 | SEQ ID NO: 24 |
| Set-5 | SEQ ID NO: 25 | SEQ ID NO: 26 | SEQ ID NO: 27 | SEQ ID NO: 28 | SEQ ID NO: 29 | SEQ ID NO: 30 |
| Set-6 | SEQ ID NO: 31 | SEQ ID NO: 32 | SEQ ID NO: 33 | SEQ ID NO: 34 | SEQ ID NO: 35 | SEQ ID NO: 36 |
| Set-7 | SEQ ID NO: 37 | SEQ ID NO: 38 | SEQ ID NO: 39 | SEQ ID NO: 40 | SEQ ID NO: 41 | SEQ ID NO: 42 |
| Set-8 | SEQ ID NO: 43 | SEQ ID NO: 38 | SEQ ID NO: 44 | SEQ ID NO: 45 | SEQ ID NO: 46 | SEQ ID NO: 42 |
| Set-9 | SEQ ID NO: 47 | SEQ ID NO: 48 | SEQ ID NO: 49 | SEQ ID NO: 50 | SEQ ID NO: 51 | SEQ ID NO: 52 |
| Set-10 | SEQ ID NO: 53 | SEQ ID NO: 48 | SEQ ID NO: 54 | SEQ ID NO: 50 | SEQ ID NO: 51 | SEQ ID NO: 52 |
| Set-11 | SEQ ID NO: 55 | SEQ ID NO: 48 | SEQ ID NO: 56 | SEQ ID NO: 50 | SEQ ID NO: 57 | SEQ ID NO: 52 |
| Set-12 | SEQ ID NO: 58 | SEQ ID NO: 59 | SEQ ID NO: 60 | SEQ ID NO: 61 | SEQ ID NO: 62 | SEQ ID NO: 63 |
| Set-13 | SEQ ID NO: 64 | SEQ ID NO: 65 | SEQ ID NO: 66 | SEQ ID NO: 67 | SEQ ID NO: 68 | SEQ ID NO: 69 |
| Set-14 | SEQ ID NO: 70 | SEQ ID NO: 65 | SEQ ID NO: 71 | SEQ ID NO: 67 | SEQ ID NO: 72 | SEQ ID NO: 69 |
| Set-15 | SEQ ID NO: 70 | SEQ ID NO: 73 | SEQ ID NO: 74 | SEQ ID NO: 75 | SEQ ID NO: 76 | SEQ ID NO: 77 |
| Set-16 | SEQ ID NO: 78 | SEQ ID NO: 73 | SEQ ID NO: 79 | SEQ ID NO: 80 | SEQ ID NO: 81 | SEQ ID NO: 82 |

TABLE 2-continued

LAMP Primer Sets

| Set | F3 | B3 | FIP | BIP | LF | LB |
|---|---|---|---|---|---|---|
| Set-17 | SEQ ID NO: 83 | SEQ ID NO: 84 | SEQ ID NO: 85 | SEQ ID NO: 86 | SEQ ID NO: 87 | SEQ ID NO: 88 |
| Set-18 | SEQ ID NO: 89 | SEQ ID NO: 90 | SEQ ID NO: 91 | SEQ ID NO: 92 | SEQ ID NO: 93 | SEQ ID NO: 94 |
| Set-19 | SEQ ID NO: 95 | SEQ ID NO: 96 | SEQ ID NO: 97 | SEQ ID NO: 98 | SEQ ID NO: 93 | SEQ ID NO: 99 |
| Set-20 | SEQ ID NO: 89 | SEQ ID NO: 100 | SEQ ID NO: 101 | SEQ ID NO: 102 | SEQ ID NO: 103 | SEQ ID NO: 104 |
| Set-21 | SEQ ID NO: 89 | SEQ ID NO: 100 | SEQ ID NO: 101 | SEQ ID NO: 105 | SEQ ID NO: 103 | SEQ ID NO: 104 |
| Set-22 | SEQ ID NO: 58 | SEQ ID NO: 59 | SEQ ID NO: 106 | SEQ ID NO: 61 | SEQ ID NO: 62 | SEQ ID NO: 63 |
| Set-23 | SEQ ID NO: 107 | SEQ ID NO: 59 | SEQ ID NO: 108 | SEQ ID NO: 61 | SEQ ID NO: 109 | SEQ ID NO: 63 |
| Set-24 | SEQ ID NO: 107 | SEQ ID NO: 59 | SEQ ID NO: 110 | SEQ ID NO: 61 | SEQ ID NO: 109 | SEQ ID NO: 63 |
| Set-25 | SEQ ID NO: 111 | SEQ ID NO: 59 | SEQ ID NO 112 | SEQ ID NO: 61 | SEQ ID NO: 109 | SEQ ID NO: 63 |
| Set-26 | SEQ ID NO: 113 | SEQ ID NO: 114 | SEQ ID NO: 115 | SEQ ID NO: 116 | SEQ ID NO: 117 | SEQ ID NO: 118 |
| Set-27 | SEQ ID NO: 119 | SEQ ID NO: 120 | SEQ ID NO: 121 | SEQ ID NO: 122 | SEQ ID NO: 123 | SEQ ID NO: 124 |
| Set-28 | SEQ ID NO: 125 | SEQ ID NO: 126 | SEQ ID NO: 127 | SEQ ID NO: 128 | SEQ ID NO: 129 | SEQ ID NO: 130 |
| Set-29 | SEQ ID NO: 131 | SEQ ID NO: 126 | SEQ ID NO: 132 | SEQ ID NO: 133 | SEQ ID NO: 134 | SEQ ID NO: 130 |

Typically, 3 to 5 µL of nucleic acid extracted from a human urine sample or from buffer spiked with in-house in vitro transcribed HsActB RNA or negative controls (NTC=nuclease free water or Tris buffer, no template control) served as template for RTLAMP reactions. 10-25 µl total volume reactions were prepared on ice as mixes containing formulations including 1× amplification buffer comprising 10-40 mM Tris-HCl, 0-0.5% Tween 20, 0-300 mM Trehalose, 5-70 mM KCl, 4-41 mM $MgSO_4$, 10-20 mM $(NH_4)_2SO_4$, 0-2 mM TCEP and 1.6-2 mM each dCTP, dGTP, dATP and dTTP. NEB Bst2 polymerase (NEB CN #M0537L) and RTx Warmstart reverse transcriptase (NEB CN #M0380S) enzymes. Primers (2 µM inner primers, 0.2 µM outer primers, and 0.8 µM Loop primers) were added to individual reactions or directly to master mixes as required per experimental design. Molecular beacons (0.2 µM) or 200 nM Yo-Pro-1, Yo-Pro-3 or To-Pro dye was also added to the master mix, as indicated in the examples below. Amplification reactions were prepared with the standard 6-primer. Master mixes were distributed to individual sample templates, vortexed and centrifuged briefly and each reaction loaded into individual wells of a 96 or 384 well plate (Roche CN #4729692001 or BioRad CNhsI9605). Reactions were carried out at temperatures ranging from 60-67° C. and fluorescence monitored on either a Roche LightCycler 96 Real-Time PCR instrument or a BioRad CFX96 real time cycler. Target amplification was monitored via intercalating dye or molecular beacon probe binding to target resulting in release of molecular beacon fluorescence intramolecular quenching.

Example 2

LAMP with Dye Detection

A negative urine matrix that naturally contains endogenous human B-actin was extracted using standard extraction methods and the sample was amplified using LAMP primers (as described in Table 2). YoPro™ dye or a compatible wavelength version within the same dye set family (Life Technologies; green fluorescent carbocyanine nucleic acid stain) was used for the detection of the amplified product. The master mix was prepared as described in Example 1. Results are summarized in Table 3, in which the Time to Positive (Tp) was calculated using an in house developed algorithm.

TABLE 3

Time to Positive Dye Detection

| Primer Set | Urine | NTC |
|---|---|---|
| Set-1 | 7.95 | 16.3 |
| Set-2 | 5.41 | negative |
| Set-3 | 7.95 | 19.6 |
| Set-4 | 7.81 | negative |
| Set-5 | negative | negative |
| Set-6 | 4.51 | negative |
| Set-7 | 7.25 | negative |
| Set-8 | 4.43 | negative |
| Set-9 | 13.04 | negative |
| Set-10 | 11.9 | negative |
| Set-11 | 13.32 | negative |
| Set-12 | 5.42 | negative |
| Set-13 | 9.79 | negative |
| Set-14 | 11.9 | negative |
| Set-15 | 11.91 | negative |
| Set-16 | 15.87 | negative |
| Set-17 | negative | negative |
| Set-18 | 8.8 | negative |
| Set-19 | negative | negative |
| Set-20 | negative | negative |
| Set-21 | 11.86 | negative |
| Set-22 | 6.54 | 27.88 |
| Set-23 | 6.47 | 24.16 |
| Set-24 | 6.435 | 28.82 |
| Set-25 | 5.28 | 25.63 |
| Set-26 | 13.31 | negative |
| Set-27 | negative | negative |
| Set-28 | 7.25 | negative |
| Set-29 | 6.05 | negative |

Example 3

Molecular Beacon Detection

To provide an additional level of direct sequence based detection of amplified product (as opposed to indirect dye detection), molecular beacons (MB1-50) targeting unique nucleotides within the β-actin amplicon of primer sets with promising Tp's combined with sensitivity, were designed (SEQ ID NOs: 135-184) and utilized for detection of amplification from nucleic acid extracted from live bacteria (Table 4). The molecular beacon probe was designed with 5' fluorophore/3' quencher modifications (6-Carboxyfluorescein (FAM)) and Black Hole Quencher 1 (BHQ1) included to provide target-specific fluorescent detection. Molecular Beacons MB49 and MB50 (SEQ ID NOs: 183 & 184) include LNA nucleotides as indicated by "[+X]", where X indicates the identity of the nucleobase.

TABLE 4

Probe Sequences

| ID | Fluor | Quench | Sequence (5' to 3') | Sequence ID |
|---|---|---|---|---|
| MB1 | FAM | BHQ1 | CGCGTGCACTCTTCCAGCCTTCCTTCCTGGGCACGCG | SEQ ID NO: 135 |
| MB2 | FAM | BHQ1 | CGCGTGGCATGGAGTCCTGTGGCATCCACGCG | SEQ ID NO: 136 |
| MB3 | FAM | BHQ1 | CGCGATCGATCGGCGGCTCCATCCTGGATCGCG | SEQ ID NO: 137 |
| MB4 | FAM | BHQ1 | CGACCAGGATCGGCGGCTCCATCCTGCTGGTCG | SEQ ID NO: 138 |
| MB5 | FAM | BHQ1 | CCGTGTGGATCGGCGGCTCCATCCTGCACACGG | SEQ ID NO: 139 |
| MB6 | FAM | BHQ1 | CCGATGGGATCGGCGGCTCCATCCTGCCATCGG | SEQ ID NO: 140 |
| MB7 | FAM | BHQ1 | CGCGATCAGATGTGGATCAGCAAGCAGGAGGATCGCG | SEQ ID NO: 141 |
| MB8 | FAM | BHQ1 | CGTACGCAGATGTGGATCAGCAAGCAGGAGGCGTACG | SEQ ID NO: 142 |
| MB9 | FAM | BHQ1 | CGGCCTAAGATGTGGATCAGCAAGCAGGAGTAGGCCG | SEQ ID NO: 143 |
| MB10 | FAM | BHQ1 | CGCGATCTACCACTGGCATCGTGATGGACTGATCGCG | SEQ ID NO: 144 |
| MB11 | FAM | BHQ1 | CCGCTCGTACCACTGGCATCGTGATGGACTCGAGCGG | SEQ ID NO: 145 |
| MB12 | FAM | BHQ1 | CCGCGGATACCACTGGCATCGTGATGGACTTCCGCGG | SEQ ID NO: 146 |
| MB13 | FAM | BHQ1 | CGTCCAGCCAGATCATGTTTGACTGGACG | SEQ ID NO: 147 |
| MB14 | FAM | BHQ1 | CGTCCAGAGATCATGTTTGAGACCCTGGACG | SEQ ID NO: 148 |
| MB15 | FAM | BHQ1 | CGAGGTCCAGATCATGTTTGAGACCTCG | SEQ ID NO: 149 |
| MB16 | FAM | BHQ1 | CGCTGAGTCATGTTTGAGACCCTCAGCG | SEQ ID NO: 150 |
| MB17 | FAM | BHQ1 | CGCGATCGTCCACCTTCCAGCAGATGTGGATCGCG | SEQ ID NO: 151 |
| MB18 | FAM | BHQ1 | CCGCGAGAAGATGACCCAGATCATCTCGCGG | SEQ ID NO: 152 |
| MB19 | FAM | BHQ1 | CCTCGAGAAGATGACCCAGATCATCTCGAGG | SEQ ID NO: 153 |
| MB20 | FAM | BHQ1 | CCGCGAGAAGATGACCCAGATCACTCGCGG | SEQ ID NO: 154 |
| MB21 | FAM | BHQ1 | CGCGATCGACCCAGATCATGTTTGAGGATCGCG | SEQ ID NO: 155 |
| MB22 | FAM | BHQ1 | CGTCGGTGACCCAGATCATGTTTGAGACCGACG | SEQ ID NO: 156 |
| MB23 | FAM | BHQ1 | CGCGATCACATGCCGGAGCCGTTGTCGAGATCGCG | SEQ ID NO: 157 |
| MB24 | FAM | BHQ1 | CCGATGGACATGCCGGAGCCGTTGTCGACCATCGG | SEQ ID NO: 158 |
| MB25 | FAM | BHQ1 | CGCGATCCGCCAGCTCACCATGGATCGCG | SEQ ID NO: 159 |
| MB26 | FAM | BHQ1 | CAGGTCTCGCCAGCTCACCATGAGACCTG | SEQ ID NO: 160 |
| MB27 | FAM | BHQ1 | CGCGATCTTCCCCTCCATCGTGATCGCG | SEQ ID NO: 161 |
| MB28 | FAM | BHQ1 | CACCGTCTTCCCCTCCATCGTGACGGTG | SEQ ID NO: 162 |
| MB29 | FAM | BHQ1 | CGCGATCCCTGTGGCATCCACGAAACTAGATCGCG | SEQ ID NO: 163 |
| MB30 | FAM | BHQ1 | CCGGAGTCCTGTGGCATCCACGAAACTAACTCCGG | SEQ ID NO: 164 |
| MB31 | FAM | BHQ1 | CCGCGAAGATGACCCAGATCATGTTCGCGG | SEQ ID NO: 165 |
| MB32 | FAM | BHQ1 | CCGCGAAGATGACCCAGATCATGTTTCGCGG | SEQ ID NO: 166 |
| MB33 | FAM | BHQ1 | CGGCGATGACCCAGATCATGATCGCCG | SEQ ID NO: 167 |
| MB34 | FAM | BHQ1 | CGCGAAGATGACCCAGATCATGCTTCGCG | SEQ ID NO: 168 |
| MB35 | FAM | BHQ1 | CAAGCCGATGACCCAGATCATGCGGCTTG | SEQ ID NO: 169 |
| MB36 | FAM | BHQ1 | CCGATGGACTCCGGTGACGGGGCCATCGG | SEQ ID NO: 170 |
| MB37 | FAM | BHQ1 | CGTCGGTGACCCAGATCATGTTTGAGACACCGACG | SEQ ID NO: 171 |
| MB38 | FAM | BHQ1 | CGGCCTGACCCAGATCATGTTTGAGACAGGCCG | SEQ ID NO: 172 |

TABLE 4-continued

Probe Sequences

| ID | Fluor | Quench | Sequence (5' to 3') | Sequence ID |
|---|---|---|---|---|
| MB39 | FAM | BHQ1 | CGGCGGTGACCCAGATCATGTTTGAGACCGCCG | SEQ ID NO: 173 |
| MB40 | FAM | BHQ1 | CGGCGATGACCCAGATCATGTTTGAGATCGCCG | SEQ ID NO: 174 |
| MB41 | FAM | BHQ1 | CAGCGGTGACCCAGATCATGTTTGAGACCGCTG | SEQ ID NO: 175 |
| MB42 | FAM | BHQ1 | CGCGGTGACCCAGATCATGTTTGAGACCCACCGCG | SEQ ID NO: 176 |
| MB43 | FAM | BHQ1 | CGGCACCAACTGGGACGACATGGGGTGCCG | SEQ ID NO: 177 |
| MB44 | FAM | BHQ1 | CGGCACCAACTGGGACGACATGGAGAAAATCTGGTGCCG | SEQ ID NO: 178 |
| MB45 | FAM | BHQ1 | CGACCCCATCGAGCACGGCATCGTCACGGGGTCG | SEQ ID NO: 179 |
| MB46 | FAM | BHQ1 | CCATGGGTCAGAAGGATTCCTATGTGGCCCATGG | SEQ ID NO: 180 |
| MB47 | FAM | BHQ1 | CGGCCGACATGGAGAAAATCTGGCACCACACCTCGGCCG | SEQ ID NO: 181 |
| MB48 | FAM | BHQ1 | CCGGGTCAGAAGGATTCCTATGTGGGCGACCCGG | SEQ ID NO: 182 |
| MB49 | FAM | BHQ1 | CACGGGTCGACC[+C]AGA[+T]CA[+T]GTT[+T]GAGACCCGTG | SEQ ID NO: 183 |
| MB50 | FAM | BHQ1 | CACGCGTGACC[+C]AGA[+T]CA[+T]GTT[+T]GAGACGCGTG | SEQ ID NO: 184 |

10-25 μL total volume reactions were evaluated utilizing eluate from a negative urine matrix that contains naturally occurring endogenous human β-actin as template input according to the methods described in Examples 1 and 2. While use of a Molecular Beacon for detection resulted in a slight increase in reaction Tp, the ability to directly detect amplification products based on sequence, and thereby distinguish closely related species, provides a reasonable tradeoff.

TABLE 5

Time to Positive (Probe Detection)

| Primers | Beacon | Tp w/ beacon | Tp for NTC |
|---|---|---|---|
| Set-1 | SEQ ID NO: 136 | 10.03 | — |
| Set-2 | SEQ ID NO: 135 | 10.42 | — |
| Set-3 | SEQ ID NO: 137 | 15.16 | — |
| Set-3 | SEQ ID NO: 138 | 14.70 | — |
| Set-3 | SEQ ID NO: 139 | 12.79 | — |
| Set-3 | SEQ ID NO: 140 | 10.91 | — |
| Set-3 | SEQ ID NO: 141 | 12.57 | — |
| Set-3 | SEQ ID NO: 142 | 13.38 | — |
| Set-3 | SEQ ID NO: 143 | 13.95 | — |
| Set-3 | SEQ ID NO: 151 | 11.13 | — |
| Set-6 | SEQ ID NO: 181 | 8.78 | — |
| Set-6 | SEQ ID NO: 182 | 8.90 | — |
| Set-8 | SEQ ID NO: 177 | 7.94 | — |
| Set-8 | SEQ ID NO: 178 | 7.68 | — |
| Set-8 | SEQ ID NO: 179 | 7.12 | — |
| Set-8 | SEQ ID NO: 180 | 8.47 | — |
| Set-12 | SEQ ID NO: 144 | 10.59 | — |
| Set-12 | SEQ ID NO: 145 | 8.34 | — |
| Set-12 | SEQ ID NO: 146 | 9.80 | — |
| Set-12 | SEQ ID NO: 147 | 13.00 | — |
| Set-12 | SEQ ID NO: 148 | 11.80 | — |
| Set-12 | SEQ ID NO: 149 | 11.16 | — |
| Set-12 | SEQ ID NO: 150 | 11.51 | — |
| Set-13 | SEQ ID NO: 157 | 11.25 | 50.07 |
| Set-13 | SEQ ID NO: 158 | 11.86 | — |
| Set-13 | SEQ ID NO: 159 | 16.05 | — |
| Set-13 | SEQ ID NO: 160 | 18.66 | — |
| Set-13 | SEQ ID NO: 161 | 17.28 | 27.26 |
| Set-13 | SEQ ID NO: 162 | 14.92 | — |
| Set-18 | SEQ ID NO: 163 | 10.62 | 42.32 |
| Set-18 | SEQ ID NO: 164 | 11.27 | — |
| Set-22 | SEQ ID NO: 144 | 10.45 | 36.48 |
| Set-22 | SEQ ID NO: 145 | 8.75 | 40.97 |
| Set-22 | SEQ ID NO: 146 | 9.81 | — |
| Set-22 | SEQ ID NO: 148 | 11.74 | 42.13 |
| Set-22 | SEQ ID NO: 152 | 11.78 | — |
| Set-22 | SEQ ID NO: 153 | 13.77 | 14.72 |
| Set-22 | SEQ ID NO: 154 | 13.68 | 47.92 |
| Set-22 | SEQ ID NO: 155 | 12.14 | 45.17 |
| Set-22 | SEQ ID NO: 156 | 12.19 | — |
| Set-22 | SEQ ID NO: 170 | 9.45 | — |
| Set-25 | SEQ ID NO: 144 | 11.55 | 42.02 |
| Set-25 | SEQ ID NO: 145 | 9.77 | 41.11 |
| Set-25 | SEQ ID NO: 146 | 10.34 | — |
| Set-25 | SEQ ID NO: 148 | 12.82 | 24.08 |
| Set-25 | SEQ ID NO: 152 | 12.18 | — |
| Set-25 | SEQ ID NO: 153 | 14.80 | 16.33 |
| Set-25 | SEQ ID NO: 154 | 14.39 | — |
| Set-25 | SEQ ID NO: 155 | 13.64 | — |
| Set-25 | SEQ ID NO: 156 | 8.99 | — |
| Set-29 | SEQ ID NO: 145 | 14.77 | — |
| Set-29 | SEQ ID NO: 152 | 10.48 | 17.81 |
| Set-29 | SEQ ID NO: 153 | 10.69 | — |
| Set-29 | SEQ ID NO: 154 | 10.02 | — |
| Set-29 | SEQ ID NO: 155 | 12.99 | — |
| Set-29 | SEQ ID NO: 156 | 7.69 | — |
| Set-29 | SEQ ID NO: 165 | 12.98 | 20.93 |
| Set-29 | SEQ ID NO: 166 | 9.76 | — |
| Set-29 | SEQ ID NO: 167 | 13.98 | — |
| Set-29 | SEQ ID NO: 168 | 14.26 | — |
| Set-29 | SEQ ID NO: 169 | 13.72 | — |
| Set-29 | SEQ ID NO: 171 | 8.63 | 25.44 |
| Set-29 | SEQ ID NO: 172 | 8.41 | — |
| Set-29 | SEQ ID NO: 173 | 7.37 | — |
| Set-29 | SEQ ID NO: 174 | 7.68 | 25.79 |
| Set-29 | SEQ ID NO: 175 | 7.80 | — |
| Set-29 | SEQ ID NO: 176 | 8.31 | — |
| Set-29 | SEQ ID NO: 183 | 9.89 | — |
| Set-29 | SEQ ID NO: 184 | 9.17 | — |

Although the foregoing invention has been described in some detail by way of illustration and example for purposes of clarity of understanding, it is readily apparent to those of ordinary skill in the art in light of the teachings of this invention that certain changes and modifications can be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

The invention claimed is:

1. A composition comprising a set of primers comprising set-29, wherein set-29 comprises primer sequences of SEQ ID NO: 132 and SEQ ID NO: 133.

2. The composition of claim 1, further comprising a probe.

3. The composition at claim 1, further comprising a labeled probe, wherein the probe sequence comprises SEQ ID NO:184.

4. The composition of claim 2, wherein the probe is a molecular beacon comprising a fluorophore and a quencher.

5. A molecular beacon probe comprising a fluorophore and a quencher, wherein the probe sequence comprises SEQ ID NO: 184.

6. A kit comprising a composition according to claim 1.

7. A method of detecting β-actin in a test sample, the method comprising:

(a) extracting nucleic acid from the test sample;
(b) amplifying a target sequence by reacting nucleic acid extracted in step (a) for less than ten minutes with a reaction mixture comprising a strand displacement DNA polymerase and a sequence-specific isothermal loop mediated amplification (LAMP) primer set; and
(c) detecting the presence or absence of an amplified product of step (b); wherein the presence of said amplification product is indicative of the presence of β-actin in the test sample, wherein said sequence-specific LAMP primer set is set-29, wherein set-29 comprises primer sequences of SEQ ID NO: 132 and SEQ ID NO: 133.

8. The method of claim 7, wherein detecting the presence or absence of the amplification product comprises hybridizing the amplified product with a molecular beacon probe, wherein the probe sequence comprises SEQ ID NO: 184.

* * * * *

SEQUENCE LISTING

```
<160> NUMBER OF SEQ ID NOS: 184

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gagctacgag ctgcctga                                                       18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tctgcatcct gtcggcaa                                                       18

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccaggaagga aggctggaag agtcggccag gtcatcacca t                             41

<210> SEQ ID NO 4
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctgtggcatc cacgaaacta ccttctgtgt tggcgtacag gtct                          44

<210> SEQ ID NO 5
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cggaaccgct cattgcca                                                    18

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcatgaagtg tgacgtggac atc                                              23

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aagagatggc cacggctg                                                    18

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
atgaagtgtg acgtggacat g                                                21

<210> SEQ ID NO 9
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcggaaccgc tcattgccaa gctcctccct ggagaaga                              38

<210> SEQ ID NO 10
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
actcttccag ccttccttcc tggatggagt tgaaggtagt ttcgtg                     46

<210> SEQ ID NO 11
<211> LENGTH: 19
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 11
gtgatgacct ggccgtcag                                              19

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcatggagtc ctgtggcatc                                             20

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
caggatgcag aaggagat                                               18

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtgtaacgca actaagtcat                                             20

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ccacacggag tacttgcgcc agcacaatga agatcaa                          37

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccagcagatg tggatcagcc tagaagcatt tgcggtg                          37

<210> SEQ ID NO 17
<211> LENGTH: 19
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 17
ctcaggagga gcaatgatc                                                      19

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aagcaggagt atgacgagt                                                      19

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
acccagatca tgtttgaga                                                      19

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
atctcttgct cgaagtcc                                                       18

<210> SEQ ID NO 21
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
catcacgatg ccagtggtac catgtacgtt gctatccag                                39

<210> SEQ ID NO 22
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
catgaagatc ctcaccgagc ctccttaatg tcacgcac                                 38

<210> SEQ ID NO 23
<211> LENGTH: 18
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 23
cagaggcgta cagggata                                                   18

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ctacagcttc accaccac                                                   18

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atccacgaaa ctaccttca                                                  19

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gatccacacg gagtactt                                                   18

<210> SEQ ID NO 27
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ccagacagca ctgtgttggc catcatgaag tgtgacg                              37

<210> SEQ ID NO 28
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
acaggatgca gaaggagatc acaggaggag caatgatct                            39

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 29
caggtctttg cggatgtc                                                   18

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cacccagcac aatgaagat                                                  19

<210> SEQ ID NO 31
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gtgatggtgg gcatgg                                                     16

<210> SEQ ID NO 32
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tgggtcatct tctcgc                                                     16

<210> SEQ ID NO 33
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gtgacgatgc cgtgctctca gaaggattcc tatgtgg                              37

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
aactgggacg acatggagac acacgcagct cattg                                35

<210> SEQ ID NO 35
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 35
ggtgaggatg cctctc                                                   16

<210> SEQ ID NO 36
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tctggcacca caccTT                                                   16

<210> SEQ ID NO 37
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37 cttccctcc atcgtg                                                    16

<210> SEQ ID NO 38
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cacacgcagc tcattg                                                   16

<210> SEQ ID NO 39
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tgaggatgcc tctcttgctc gtgatggtgg gcat                               34

<210> SEQ ID NO 40
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ccatcgagca cggcatcgaa ggtgtggtgc ca                                 32

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 41
cacataggaa tccttctgac c                                              21

<210> SEQ ID NO 42
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ctgggacgac atggaga                                                   17

<210> SEQ ID NO 43
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cgtgatggtg ggcat                                                     15

<210> SEQ ID NO 44
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gggtacttca gggtgaggat cagaaggatt cctatgtgg                           39

<210> SEQ ID NO 45
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gagcacggca tcgtcacgaa ggtgtggtgc ca                                  32

<210> SEQ ID NO 46
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tgcctctctt gctctgg                                                   17

<210> SEQ ID NO 47
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
```

-continued gagaggcatc ctcacc                                                     16

<210> SEQ ID NO 48
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gtagatgggc acagtgt                                                    17

<210> SEQ ID NO 49
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ccacacgcag ctcattgtaa tcgagcacgg catc                                 34

<210> SEQ ID NO 50
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tgctatccag gctgtgctaa gtccatcacg atgcc                                35

<210> SEQ ID NO 51
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
aaggtgtggt gccaga                                                     16

<210> SEQ ID NO 52
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ctctggccgt accact                                                     16

<210> SEQ ID NO 53
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
atcgagcacg gcatc                                                                15

<210> SEQ ID NO 54
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ccacacgcag ctcattgtgg gacgacatgg agaaa                                          35

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
tcagaaggat tcctatgtgg                                                           20

<210> SEQ ID NO 56
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tctccatgtc gtcccagttg agaggcatcc tcacc                                          35

<210> SEQ ID NO 57
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
tgacgatgcc gtgct                                                                15

<210> SEQ ID NO 58
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
accgcgagaa gatgac                                                               16

<210> SEQ ID NO 59
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gacgcaggat ggcat                                                                15

```
<210> SEQ ID NO 60
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ccagaggcgt acagggattc atgtttgaga ccttcaac                                  38

<210> SEQ ID NO 61
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
cgtaccactg gcatcgtggt agatgggcac agtgt                                     35

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cacagcctgg atagcaac                                                        18

<210> SEQ ID NO 63
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
atggactccg gtgacg                                                          16

<210> SEQ ID NO 64
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
tcgcctttgc cgatc                                                           15

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ggaatccttc tgacccat                                                        18
```

<210> SEQ ID NO 66
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
catgccggag ccgttgcgcc agctcaccat g                              31

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ttcgcgggcg acgatcatca cgccctggtg                                30

<210> SEQ ID NO 68
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gcgcggcgat atcatc                                               16

<210> SEQ ID NO 69
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gtcttcccct ccatcgt                                              17

<210> SEQ ID NO 70
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
cgagcacaga gcctc                                                15

<210> SEQ ID NO 71
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cgagcgcggc gatatcgcct ttgccgatcc g                              31

```
<210> SEQ ID NO 72
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
catccatggt gagctgg                                                        17

<210> SEQ ID NO 73
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gatgccgtgc tcgat                                                          15

<210> SEQ ID NO 74
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ccggccttgc acatgccgcc agctcaccat g                                        31

<210> SEQ ID NO 75
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
cgtgatggtg ggcatggggt gaggatgcct ctc                                      33

<210> SEQ ID NO 76
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
tgtcgacgac gagcg                                                          15

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gtcagaagga ttcctatgtg g                                                   21

<210> SEQ ID NO 78
```

```
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
cgccagctca ccatg                                                      15

<210> SEQ ID NO 79
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
catcacgccc tggtgctcgt cgtcgacaac g                                    31

<210> SEQ ID NO 80
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ggtcagaagg attcctatgt ggggtgagga tgcctctc                             38

<210> SEQ ID NO 81
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ccggccttgc acatg                                                      15

<210> SEQ ID NO 82
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
cgaggcccag agcaa                                                      15

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
atgagctgcg tgtggctccc                                                 20

<210> SEQ ID NO 84
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gggcataccc ctcgtagatg gg                                            22

<210> SEQ ID NO 85
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
agcacagcct ggatagcaac gtacaccaag gccaaccgcg agaag                   45

<210> SEQ ID NO 86
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
atccctgtac gcctctggcc gtaccagtgt gggtgacccc gtca                    44

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
tggctggggt gttgaaggtc tca                                           23

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
cactggcatc gtgatggact ccg                                           23

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
ctggacttcg agcaagagat ggc                                           23

<210> SEQ ID NO 90
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 90
tgttggcgta caggtctttg cg                                                  22

<210> SEQ ID NO 91
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
aagagtgcct cagggcagcg gaaggagaag agctacgagc tgcct                         45

<210> SEQ ID NO 92
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
ccagccttcc ttcctgggca tggaccacgt cacacttcat gatggagtt                     49

<210> SEQ ID NO 93
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
gctcattgcc aatggtgatg acctg                                               25

<210> SEQ ID NO 94
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
cctgtggcat ccacgaaact acctt                                               25

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
acggctgctt ccagctcctc                                                     20

<210> SEQ ID NO 96
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 96
gacagcactg tgttggcgta ca                                              22

<210> SEQ ID NO 97
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
aagagtgcct cagggcagcg gaaagctacg agctgcctga cgg                       43

<210> SEQ ID NO 98
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
agccttcctt cctgggcatg gagtcccacg tcacacttca tgatggagt                 49

<210> SEQ ID NO 99
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
tgtggcatcc acgaaactac cttca                                           25

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
gcggatgtcc acgtcacact tc                                              22

<210> SEQ ID NO 101
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
ccaatggtga tgacctggcc gtcagacggc tgcttccagc tcctc                     45

<210> SEQ ID NO 102
<211> LENGTH: 43
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 102
atgagcggtt ccgctgccct gatcgtggat gccacaggac tcc            43

<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gcagctcgta gctcttctcc agg                                   23

<210> SEQ ID NO 104
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
gcactcttcc agccttcctt cctg                                  24

<210> SEQ ID NO 105
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
atgagcggtt ccgctgccct gagatgccac aggactccat gcc            43

<210> SEQ ID NO 106
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
ccagaggcgt acagggatcc agatcatgtt tgagacc                    37

<210> SEQ ID NO 107
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
ccaaccgcga gaagat                                           16

<210> SEQ ID NO 108
<211> LENGTH: 38
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 108
agaggcgtac agggatagca cccagatcat gtttgaga           38

<210> SEQ ID NO 109
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
atagcaacgt acatggctg                                19

<210> SEQ ID NO 110
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
agaggcgtac agggatagcg acccagatca tgtttgag           38

<210> SEQ ID NO 111
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
ccaaccgcga gaaga                                    15

<210> SEQ ID NO 112
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
gaggcgtaca gggatagcat gacccagatc atgtttga           38

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
ttctacaatg agctgcgtgt                               20

<210> SEQ ID NO 114
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
cggagtccat cacgatgc                                                      18

<210> SEQ ID NO 115
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
aaggtctcaa acatgatctg ggtcacgtgc tgctgaccga g                             41

<210> SEQ ID NO 116
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
ccagccatgt acgttgctat ccaagtggta cggccagagg                               40

<210> SEQ ID NO 117
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
tcgcggttgg ccttgg                                                        16

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
ggctgtgcta tccctgtacg                                                    20

<210> SEQ ID NO 119
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
aatctggcac cacaccttc                                                     19

<210> SEQ ID NO 120
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 120
aggcgtacag ggatagca                                                    18

<210> SEQ ID NO 121
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
ttggccttgg ggttcagggg agctgcgtgt ggctc                                 35

<210> SEQ ID NO 122
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
gcgagaagat gacccagatc atgtgcctgg atagcaacgt acat                       44

<210> SEQ ID NO 123
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
gcctcggtca gcagca                                                      16

<210> SEQ ID NO 124
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
agaccttcaa caccccagc                                                   19

<210> SEQ ID NO 125
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
gcacggcatc gtcacc                                                      16

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
```
gcctggatag caacgtacat                                           20

<210> SEQ ID NO 127
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
agccacacgc agctcattgt aactgggacg acatggaga                      39

<210> SEQ ID NO 128
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
tgaaccccaa ggccaaccgc tggggtgttg aaggtctc                       38

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
agaaggtgtg gtgccagatt                                           20

<210> SEQ ID NO 130
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
cgagaagatg acccagatca tgt                                       23

<210> SEQ ID NO 131
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
acggcatcgt caccaac                                              17

<210> SEQ ID NO 132
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132

```
tgctcctcgg gagccacaga catggagaaa atctggcac                                    39
```

<210> SEQ ID NO 133
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133

```
tgaaccccaa ggccaaccgt ggggtgttga aggtctca                                     38
```

<210> SEQ ID NO 134
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134

```
gcagctcatt gtagaaggtg tg                                                      22
```

<210> SEQ ID NO 135
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 135

```
cgcgtgcact cttccagcct tccttcctgg gcacgcg                                      37
```

<210> SEQ ID NO 136
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 136

```
cgcgtggcat ggagtcctgt ggcatccacg cg                                           32
```

<210> SEQ ID NO 137
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 137

```
cgcgatcgat cggcggctcc atcctggatc gcg                                          33
```

<210> SEQ ID NO 138
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 138

```
cgaccaggat cggcggctcc atcctgctgg tcg                                          33
```

<210> SEQ ID NO 139
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 139
ccgtgtggat cggcggctcc atcctgcaca cgg                           33

<210> SEQ ID NO 140
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 140
ccgatgggat cggcggctcc atcctgccat cgg                           33

<210> SEQ ID NO 141
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 141
cgcgatcaga tgtggatcag caagcaggag gatcgcg                       37

<210> SEQ ID NO 142
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 142
cgtacgcaga tgtggatcag caagcaggag gcgtacg                       37

<210> SEQ ID NO 143
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 143
cggcctaaga tgtggatcag caagcaggag taggccg                       37

<210> SEQ ID NO 144
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 144
cgcgatctac cactggcatc gtgatggact gatcgcg                       37

<210> SEQ ID NO 145
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 145
ccgctcgtac cactggcatc gtgatggact cgagcgg                    37

<210> SEQ ID NO 146
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 146
ccgcggatac cactggcatc gtgatggact tccgcgg                    37

<210> SEQ ID NO 147
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 147
cgtccagcca gatcatgttt gactggacg                             29

<210> SEQ ID NO 148
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 148
cgtccagaga tcatgtttga gaccctggac g                          31

<210> SEQ ID NO 149
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 149
cgaggtccca gatcatgttt gagacctcg                             29

<210> SEQ ID NO 150
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 150
cgctgagtca tgtttgagac cctcagcg                              28

```
<210> SEQ ID NO 151
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 151
cgcgatcgtc caccttccag cagatgtgga tcgcg                             35

<210> SEQ ID NO 152
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 152
ccgcgagaag atgacccaga tcatctcgcg g                                 31

<210> SEQ ID NO 153
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 153
cctcgagaag atgacccaga tcatctcgag g                                 31

<210> SEQ ID NO 154
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 154
ccgcgagaag atgacccaga tcactcgcgg                                   30

<210> SEQ ID NO 155
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 155
cgcgatcgac ccagatcatg tttgaggatc gcg                               33

<210> SEQ ID NO 156
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 156
cgtcggtgac ccagatcatg tttgagaccg acg                               33

<210> SEQ ID NO 157
```

<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 157
cgcgatcaca tgccggagcc gttgtcgaga tcgcg                                35

<210> SEQ ID NO 158
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 158
ccgatggaca tgccggagcc gttgtcgacc atcgg                                35

<210> SEQ ID NO 159
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 159
cgcgatccgc cagctcacca tggatcgcg                                      29

<210> SEQ ID NO 160
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 160
caggtctcgc cagctcacca tgagacctg                                      29

<210> SEQ ID NO 161
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 161
cgcgatcttc ccctccatcg tgatcgcg                                       28

<210> SEQ ID NO 162
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 162
caccgtcttc ccctccatcg tgacggtg                                       28

<210> SEQ ID NO 163
<211> LENGTH: 35

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 163
cgcgatccct gtggcatcca cgaaactaga tcgcg                              35

<210> SEQ ID NO 164
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 164
ccggagtcct gtggcatcca cgaaactaac tccgg                              35

<210> SEQ ID NO 165
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 165
ccgcgaagat gacccagatc atgttcgcgg                                    30

<210> SEQ ID NO 166
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 166
ccgcgaagat gacccagatc atgtttcgcg g                                  31

<210> SEQ ID NO 167
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 167
cggcgatgac ccagatcatg atcgccg                                       27

<210> SEQ ID NO 168
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 168
cgcgaagatg acccagatca tgcttcgcg                                     29

<210> SEQ ID NO 169
<211> LENGTH: 29
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 169
caagccgatg acccagatca tgcggcttg                                          29

<210> SEQ ID NO 170
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 170
ccgatggact ccggtgacgg ggccatcgg                                          29

<210> SEQ ID NO 171
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 171
cgtcggtgac ccagatcatg tttgagacac cgacg                                   35

<210> SEQ ID NO 172
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 172
cggcctgacc cagatcatgt ttgagacagg ccg                                     33

<210> SEQ ID NO 173
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 173
cggcggtgac ccagatcatg tttgagaccg ccg                                     33

<210> SEQ ID NO 174
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 174
cggcgatgac ccagatcatg tttgagatcg ccg                                     33

<210> SEQ ID NO 175
<211> LENGTH: 33
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 175
cagcggtgac ccagatcatg tttgagaccg ctg                                   33

<210> SEQ ID NO 176
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 176
cgcggtgacc cagatcatgt tgagaccca ccgcg                                  35

<210> SEQ ID NO 177
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 177
cggcaccaac tgggacgaca tggggtgccg                                       30

<210> SEQ ID NO 178
<211> LENGTH: 39
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 178
cggcaccaac tgggacgaca tggagaaaat ctggtgccg                             39

<210> SEQ ID NO 179
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 179
cgaccccatc gagcacggca tcgtcacggg gtcg                                  34

<210> SEQ ID NO 180
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 180
ccatgggtca gaaggattcc tatgtggccc atgg                                  34

<210> SEQ ID NO 181
<211> LENGTH: 39
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 181
cggccgacat ggagaaaatc tggcaccaca cctcggccg                              39

<210> SEQ ID NO 182
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 182
ccgggtcaga aggattccta tgtgggcgac ccgg                                   34

<210> SEQ ID NO 183
<211> LENGTH: 34
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (13)..(13)
<223> OTHER INFORMATION: Locked nucleic acid
<220> FEATURE:
<221> NAME/KEY: modified_base
<222> LOCATION: (17)..(17)
<223> OTHER INFORMATION: Locked nucleic acid
<220> FEATURE:
<221> NAME/KEY: modified_base
<222> LOCATION: (20)..(20)
<223> OTHER INFORMATION: Locked nucleic acid
<220> FEATURE:
<221> NAME/KEY: modified_base
<222> LOCATION: (24)..(24)
<223> OTHER INFORMATION: Locked nucleic acid

<400> SEQUENCE: 183
cacgggtcga cccagatcat gtttgagacc cgtg                                   34

<210> SEQ ID NO 184
<211> LENGTH: 33
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (12)..(12)
<223> OTHER INFORMATION: Locked nucleic acid
<220> FEATURE:
<221> NAME/KEY: modified_base
<222> LOCATION: (16)..(16)
<223> OTHER INFORMATION: Locked nucleic acid
<220> FEATURE:
<221> NAME/KEY: modified_base
<222> LOCATION: (19)..(19)
<223> OTHER INFORMATION: Locked nucleic acid
<220> FEATURE:
<221> NAME/KEY: modified_base
<222> LOCATION: (23)..(23)
<223> OTHER INFORMATION: Locked nucleic acid

<400> SEQUENCE: 184
cacgcgtgac ccagatcatg tttgagacgc gtg                                    33
```